(12) United States Patent
Lyssikatos et al.

(10) Patent No.: US 6,294,552 B1
(45) Date of Patent: Sep. 25, 2001

(54) ALKYNYL-SUBSTITUTED QUINOLIN-2-ONE DERIVATIVES USEFUL AS ANTICANCER AGENTS

(75) Inventors: Joseph P. Lyssikatos, Gales Ferry; Susan D. La Greca, Old Lyme, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/628,039

(22) Filed: Jul. 27, 2000

Related U.S. Application Data

(62) Division of application No. 09/383,755, filed on Aug. 26, 1999.
(60) Provisional application No. 60/098,145, filed on Aug. 27, 1998.

(51) Int. Cl.[7] .................. A61K 31/47; C07D 215/16; C07D 215/20
(52) U.S. Cl. .................. 514/312; 546/157; 546/158
(58) Field of Search .................. 514/312; 546/157, 546/158

(56) References Cited

U.S. PATENT DOCUMENTS

| 5,747,498 | 5/1998 | Schnur | 514/259 |
| 5,968,952 | 10/1999 | Venet | 514/312 |
| 6,037,350 | 3/2000 | Venet | 514/312 |
| 6,150,377 | * 11/2000 | Lyssikatos | 514/312 |

FOREIGN PATENT DOCUMENTS

| 9716443 | 5/1997 | (WO) . |
| 9721701 | 6/1997 | (WO) . |

* cited by examiner

Primary Examiner—D. Margaret Seaman
(74) Attorney, Agent, or Firm—Peter C. Richardson; Paul H. Ginsburg; Adrian G. Looney

(57) ABSTRACT

The present invention relates to compounds of formula 1

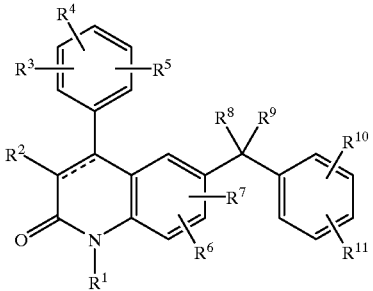

and to pharmaceutically acceptable salts, prodrugs and solvates thereof, wherein $R^1, R^2, R^3, R^4, R^5, R^6, R^7, R^8, R^9, R^{10}$, and $R^{11}$ are as defined herein. The above compounds of formula 1 are useful in the treatment of hyperproliferative disorders, such as cancer, in mammals. The invention also relates to pharmaceutical compositions containing the compounds of formula 1 and to methods of inhibiting abnormal cell growth, including cancer, in a mammal by administering the compounds of formula 1 to a mammal requiring such treatment.

6 Claims, No Drawings

ALKYNYL-SUBSTITUTED QUINOLIN-2-ONE DERIVATIVES USEFUL AS ANTICANCER AGENTS

This is a division of application Ser. No. 09/383,755, filed Aug. 26, 1999, which claims the benefit of U.S. Provisional Application No. 60/098,145, filed Aug. 27, 1998, both of which are incorporated herein by reference.

BACKGROUND OF THE INVENTION

This invention relates to a series of alkynyl-substituted quinolin-2-one derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993). The compounds of the present invention exhibit activity as inhibitors of the enzyme farnesyl protein transferase and are therefore believed to be useful as anti-cancer and anti-tumor agents. Further, the compounds of the present invention may be active against any tumors that proliferate by virtue of farnesyl protein transferase.

SUMMARY OF THE INVENTION

The present invention relates to compounds of formula 1

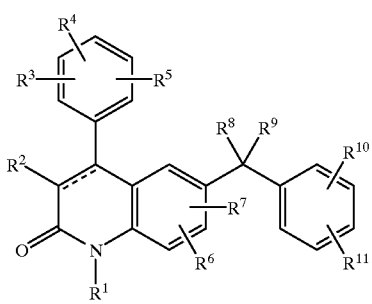

1 and to pharmaceutically acceptable salts, prodrugs and solvates thereof wherein:

the dashed line indicates that the bond between C-3 and C-4 of the quinolin-2-one ring is a single or double bond;

$R^1$ is selected from H, $C_1$–$C_{10}$ alkyl, —$(CR^{13}R^{14})_qC(O)R^{12}$, —$(CR^{13}R^{14})_qC(O)OR^{15}$, —$(CR^{13}R^{14})_qOR^{12}$, —$(CR^{13}R^{14})_qSO_2R^{15}$, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t(4$–10 membered heterocyclic), wherein t is an integer from 0 to 5 and q is an integer from 1 to 5, said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;

$R^2$ is halo, cyano, —$C(O)OR^{15}$, or a group selected from the substituents provided in the definition of $R^{12}$;

each $R^3$, $R^4$, $R^5$, $R^6$, and $R^7$ is independently selected from H, $C_1$–$C_{10}$ alkyl, $C_2$–$C_{10}$ alkenyl, halo, cyano, nitro, mercapto, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR_{12}$, —$S(O)_jR^{12}$ wherein j is an integer from 0 to 2, —$(CR^{13}R^{14})_t(C_6$–$C_{10}$ aryl), —$(CR^{13}R^{14})_t(4$–10 membered heterocyclic), —$(CR^{13}R^{14})_t(C_3$–$C_{10}$ cycloalkyl), and —$(CR^{13}R^{14})_tC\equiv CR^{16}$, and wherein in the foregoing $R^3$, $R^4$, $R^5$, $R^6$, and $R^7$ groups t is an integer from 0 to 5; the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t(4$–10 membered heterocyclic), wherein t is an integer from 0 to 5;

$R^8$ is H, —$OR^{12}$, —$NR^{12}R^{13}$, —$NR^{12}C(O)R^{13}$, cyano, —$C(O)OR^{13}$, —$SR^{12}$, —$(CR^{13}R^{14})_t(4$–10 membered heterocyclic), wherein t is an integer from 0 to 5, or $C_1$–$C_6$ alkyl, wherein said heterocyclic and alkyl moieties are optionally substituted by 1 to 3 $R^6$ substituents;

$R^9$ is —$(CR^{13}R^{14})_t$(imidazolyl) wherein t is an integer from 0 to 5 and said imidazolyl moiety is optionally substituted by 1 or 2 $R^6$ substituents;

each $R^{10}$ and $R^{11}$ is independently selected from the substituents provided in the definition of $R^6$;

each $R^{12}$ is independently selected from H, $C_1$–$C_{10}$ alkyl, —$(CR^{13}R^{14})_t(C_3$–$C_{10}$ cycloalkyl), —$CR^{13}R^{14})_t(C_6$–$C_{10}$ aryl), and —$(CR^{13}R^{14})_t(4$–10 membered heterocyclic), wherein t is from 0 to 5; said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each $R^{13}$ and $R^{14}$ is independently H or $C_1$–$C_6$ alkyl, and where $R^{13}$ and $R^{14}$ are as —$(CR^{13}R^{14})_q$ or $(CR^{13}R^{14})_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$;

$R^{17}$, $R^{18}$ and $R^{19}$ are each independently selected from the substituents provided in the definition of $R^{12}$ except $R^{17}$, $R^{18}$ and $R^{19}$ are not H; and provided that at least one of $R^3$, $R^4$ and $R^5$ is —$(CR^{13}R^{14})_tC\equiv CR^{16}$ wherein t is an integer from 0 to 5 and $R^{13}$, $R^{14}$, and $R^{16}$ are as defined above.

Preferred compounds of formula 1 include those wherein $R^1$ is H, $C_1$–$C_6$ alkyl, or cyclopropylmethyl; $R^2$ is H; $R^3$ is —$C\equiv CR^{16}$; and $R^8$ is —$NR^{12}R^{13}$, —$OR^{12}$, or a heterocyclic group selected from triazolyl, imidazolyl, pyrazolyl, and piperidinyl, wherein said heterocyclic group is optionally substituted by an $R^6$ group. More preferred compounds include those wherein $R^9$ is imidazolyl optionally substituted by $C_1$–$C_6$ alkyl; $R^8$ is hydroxy, amino, or triazolyl; and $R^4$, $R^5$, $R^{10}$ and $R^{11}$ are each independently selected from H and halo.

Other preferred compounds formula 1 include those wherein $R^1$ is —$(CR^{13}R^{14})_t(C_{13}$–$C_{10}$ cycloalkyl) wherein t is an integer from 0 to 3; $R^2$ is H; $R^3$ is —$C\equiv CR^{16}$; and $R^8$ is —$NR^{12}R^{13}$, —$OR^{12}$, or a heterocyclic group selected from triazolyl, imidazolyl, pyrazolyl, and piperidinyl, wherein said heterocyclic group is optionally substituted by an $R^6$ group. More preferred compounds include those wherein $R^9$ is imidazolyl optionally substituted by $C_1$–$C_6$ alkyl; $R^8$ is hydroxy, amino, or triazolyl; $R^4$, $R^5$, $R^{10}$ and $R^{11}$ are each independently selected from H and halo; and $R^1$ is cyclopropylmethyl.

Other preferred compounds formula 1 include those wherein $R^3$ is ethynyl and the other substituents are as defined above.

Specific preferred compounds include the following:

6-[(4-Chloro-phenyl)-hydroxy-(3-methyl-3H-imidazol-4-yl)-methyl]-4-(3-ethynyl-phenyl)-1-methyl-1H-quinolin-2-one (enantiomer A);

6-[(4-Chloro-phenyl)-hydroxy-(3-methyl-3H-imidazol-4-yl)-methyl]-4-(3-ethynyl-phenyl)-1-methyl-1H-quinolin-2-one (enantiomer B);

6-[Amino-(4-chloro-phenyl)-(3-methyl-3H-imidazol-4-yl)-methyl]-4-(3-ethynyl-phenyl)-1-methyl-1H-quinolin-2-one (enantiomer A);

6-[Amino-(4-chloro-phenyl)-(3-methyl-3H-imidazol-4-yl)-methyl]-4-(3-ethynyl-phenyl)-1-methyl-1H-quinolin-2-one (enantiomer B);

6-[(4-Chloro-phenyl)-hydroxy-(3-methyl-3H-imidazol-4-yl)-methyl]-4-(3-ethynyl-4-fluoro-phenyl)-1-methyl-1H-quinolin-2-one;

and the pharmaceutically acceptable salts, prodrugs and solvates of the foregoing compounds, as well as stereoisomers of the foregoing compounds.

The present invention also relates to intermediates of formula 28

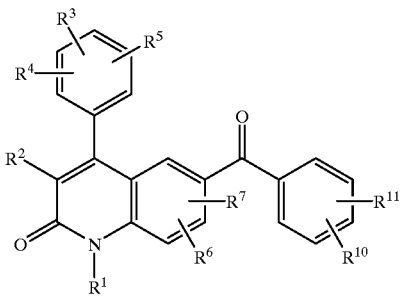

wherein $R^1$, $R^2$, $R^3$, $R^4$, $R^5$, $R^6$, $R^7$, $R^{10}$ and $R^{11}$ are as defined above.

The present invention also relates to the following specific intermediates which may be used in the preparation of the compounds of the present invention 6[(4-Chloro-phenyl)-hydroxy-(3-methyl-3H-imidazol-4-yl)-methyl]-1-methyl-4-(3-trimethylsilanylethynyl-phenyl)-1H-quinolin-2-one 6-[(4-Chloro-phenyl)-hydroxy-(2-mercapto-3-methyl-3H-imidazol-4-yl)-methyl]-1-methyl-4-(3-trimethylsilanylethynyl-phenyl)-1H-quinolin-2-one 6-(4-Chloro-benzoyl)-1-methyl-4-(3-trimethylsilanylethynyl-phenyl)-1H-quinolin-2-one 6-(4-Chloro-benzoyl)-1-methyl-4-[3-(4-trityloxy-but-1-ynyl)-phenyl]-1H-quinolin-2-one 6-(4-Chloro-benzoyl)-1-cyclopropylmethyl-4-(3-trimethylsilanylethynyl-phenyl)-1H-quinolin-2-one.

The present invention also relates to a method of preparing a compound of formula 1 wherein $R^3$ is ethynyl, which comprises treating a compound of formula 29

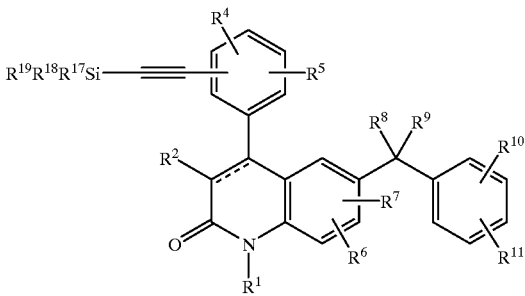

wherein $R^1$, $R^2$, $R^4$, $R^5$, $R^6$, $R^7$, $R^8$, $R^9$, $R^{10}$ and $R^{11}$ are as defined above with tetrabutylammonium fluoride.

This invention also relates to a method for the treatment of abnormal cell growth in a mammal, including a human, comprising administering to said mammal an amount of a compound of the formula 1, as defined above, or a pharmaceutically acceptable salt, prodrug or solvate thereof, that is effective in inhibiting farnesyl protein transferase. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal, including a human, comprising administering to said mammal an amount of a compound of the formula 1, as defined above, or a pharmaceutically acceptable salt, prodrug or solvate thereof, that is effective in treating abnormal cell growth.

This invention also relates to a method for the treatment of abnormal cell growth in a mammal which comprises administering to said mammal a therapeutically effective amount of a compound of formula 1, or a pharmaceutically acceptable salt, prodrug or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The present invention also relates to a method for the treatment of an infection in a mammal, including a human, that is facilitated by farnesyl protein transferase, such as hepatitis delta virus or malaria, which comprises administering to said mammal a therapeutically effective amount of a compound of formula 1 or a pharmaceutically acceptable salt, prodrug or solvate thereof.

This invention also relates to a pharmaceutical composition for the treatment of abnormal cell growth in a mammal, including a human, comprising an amount of a compound of the formula 1, as defined above, or a pharmaceutically acceptable salt, prodrug or solvate thereof, that is effective in inhibiting farnesyl protein transferase, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a pharmaceutical composition for the treatment of abnormal cell growth in a mammal, including a human, comprising an amount of a compound of the formula 1, as defined above, or a pharmaceutically acceptable salt, prodrug or solvate thereof, that is effective in treating abnormal cell growth, and a pharmaceutically acceptable carrier.

The invention also relates to a pharmaceutical composition for the treatment of abnormal cell growth in a mammal, including a human, which comprises a therapeutically effective amount of a compound of formula 1, as defined above, or a pharmaceutically acceptable salt, prodrug or solvate thereof, in combination with a pharmaceutically acceptable carrier and an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for the treatment of an infection in a mammal, including a human, that is facilitated by farnesyl protein transferase, such as malaria or hepatitus delta virus, comprising an amount of a compound of the formula 1, as defined above, or a pharmaceutically acceptable salt, prodrug or solvate thereof, that is effective in treating abnormal cell growth, and a pharmaceutically acceptable carrier.

"Abnormal cell growth", as used herein, unless otherwise indicated, refers to cell growth that is independent of normal regulatory mechanisms (e.g., loss of contact inhibition). This includes the abnormal growth of (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating"is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties.

The term "cycloalkyl", as used herein, unless otherwise indicated, includes cyclic alkyl moieties wherein alkyl is as defined above.

The term "alkenyl", as used herein, unless otherwise indicated, includes alkyl moieties having at least one carbon-carbon double bond wherein alkyl is as defined above.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms, generally 1 to 4 heteroatoms, each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

Where $R^{13}$ and $R^{14}$ are as $(CR^{13}R^{14})_q$ or $(CR^3R^{14})_t$ each is independently defined for each iteration of q or t in excess of 1. This means, for instance, that where q or t is 2 alkylene moieties of the type —$CH_2CH(CH_3)$—, and other asymmetrically branched groups, are included.

The term "pharmaceutically acceptable salt(s)", as used herein, unless otherwise indicated, includes salts of acidic or basic groups that may be present in the compounds of formula 1. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996)19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. In particular, the carbon to which the $R^8$ and $R^9$ groups are attached represents a potential chiral center; the present invention encompasses all stereoisomers based on this chiral center. The compounds of formula 1 may also exist as tautomers. This invention relates to the use of all such tautomers and mixtures thereof. Certain compounds of formula 1 may also include oxime moieties, such as where $R^3$, $R^4$, $R^5$, $R^6$ or $R^7$ is —CH=NOR$^{12}$, that exist in E or Z configurations. The present invention includes racemic mixtures of compounds of formula 1 that include such oxime moieties or specific E or Z isomers of such compounds.

DETAILED DESCRIPTION OF THE INVENTION

The compounds of formula 1 may be prepared as described below.

With reference to Scheme 1 below, the compounds of formula 1 may be prepared by hydrolysing an intermediate ether of formula 2, wherein R is $C_1$–$C_6$ alkyl, according to methods familiar to those skilled in the art, such as by stirring the intermediate of formula 2 in an aqueous acid solution. An appropriate acid is, for example, hydrochloric acid. The resulting quinolinone of formula 1 wherein $R^1$ is hydrogen may be transformed into a quinolinone wherein $R^1$ has a meaning as defined above apart from hydrogen by N-alkylation methods familiar to those skilled in the art.

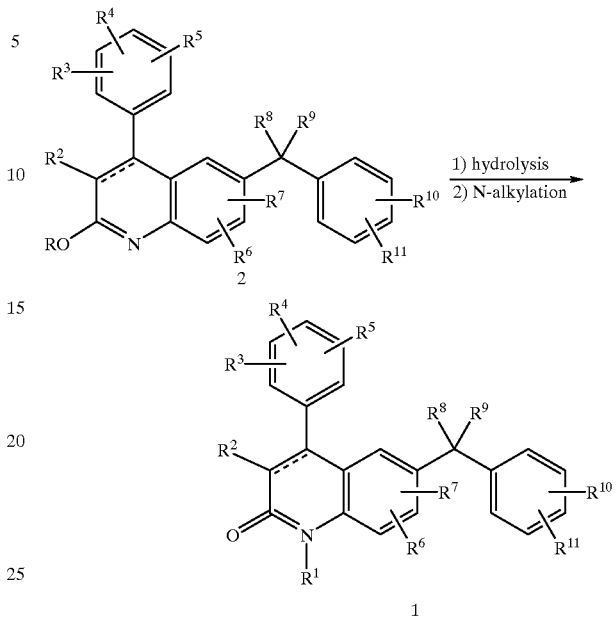

With reference to Scheme 2 below, the compounds of formula 1(b), which are compounds of formula 1 wherein $R^8$ is hydroxy, may be prepared by reacting an intermediate ketone of formula 3 with an intermediate of the formula H-$R^9$, wherein $R^9$ is as defined above and wherein in the imidazolyl moiety of said $R^9$ group a free nitrogen atom may be protected with an optional protective group, such as a sulfonyl group (for example, a dimethylamino sulfonyl group) which can be removed after the addition reaction. Said reaction requires the presence of a suitable strong base, such as sec-butyl lithium, in an appropriate solvent, such as tetrahydrofuran, and the presence of an appropriate silane derivative, such as chloro-tert-butyldimethylsilane. The silyl group can be removed with a fluoride source such as tetrabutyl ammonium fluoride. Other procedures with protective groups analogous to silane derivatives can also be applied.

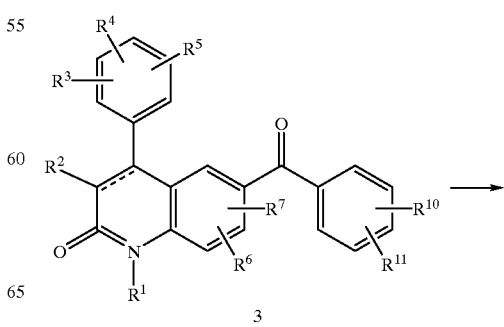

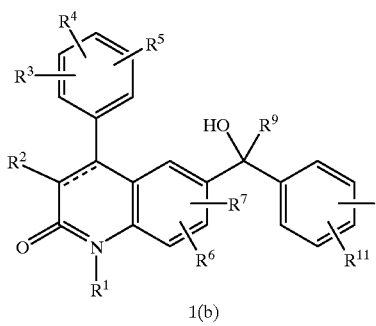

1(b)

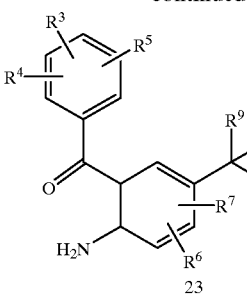

23

With reference to Scheme 3 below, compounds of formula 1(b-1), which are compounds of formula 1 wherein the dotted line is a bond and $R^1$ is hydrogen, can be prepared by reacting an intermediate of formula 21 with an intermediate of formula H-$R^9$, wherein $R^9$ is as described above. The resulting intermediate of formula 22 undergoes ring opening of the isoxazole moiety by stirring it with an acid, such as $TiCl_3$, in the presence of water. Subsequent treatment of the resulting intermediate of formula 23 with a suitable reagent, such as $R^2CH_2COCl$ or $R^2CH_2COOC_2H_5$, wherein $R^2$ is as defined above, yields either directly a compound of formula 1(b-1) or an intermediate which can be converted to a compound of formula 1(b-1) by treatment with a base, such as potassium tert-butoxide.

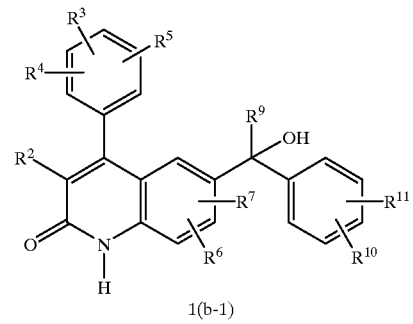

1(b-1)

Intermediates of formula 21 can be prepared by treating an intermediate of formula 16, referred to below with respect to Scheme 9, under acidic conditions.

With reference to Scheme 4 below, compounds of formula 1 wherein $R^8$ is a radical of formula —$NR^{12}R^{13}$ wherein $R^{12}$ and $R^{13}$ are as described above (said compounds are represented below by formula 1(g)), may be prepared by reacting an intermediate of formula 13, wherein W is an appropriate leaving group, such as halo, with a reagent of formula 14. Said reaction may be performed by stirring the reactants in an appropriate solvent, such as tetrahydrofuran.

Scheme 3

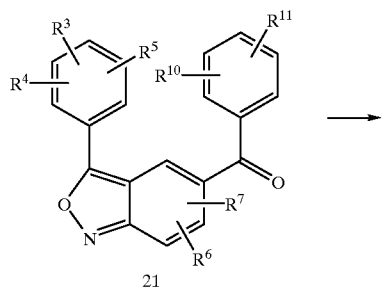

21

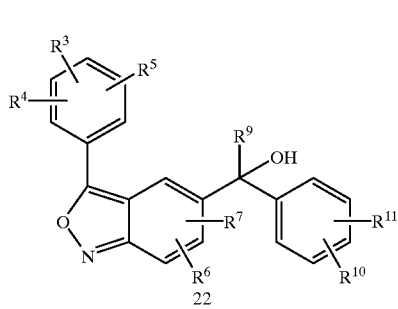

22

Scheme 4

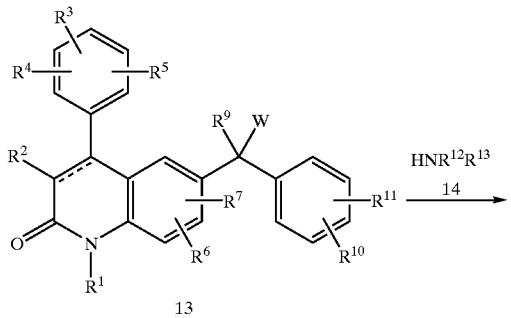

13

-continued

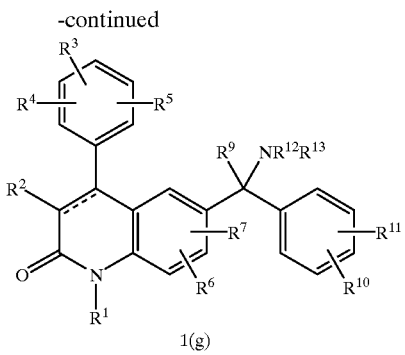

1(g)

Compounds of formula 1(g), or other embodiments of formula 1, wherein the dotted line represents a bond can be converted into compounds wherein the dotted line does not represent a bond by hydrogenation methods familiar to those skilled in the art. Compounds wherein the dotted line does not represent a bond may be converted into compounds wherein the dotted line represents a bond by oxidation methods familiar to those skilled in the art.

With reference to Scheme 5 below, compounds of formula 1 wherein $R^8$ is hydroxy (said compounds being represented by formula 1(b)) may be converted into compounds of formula 1(c), wherein $R^{12}$ has the meaning described above except it is not hydrogen, by methods known to those skilled in the art, including O-alkylation or O-acylation reactions; such as by reacting the compound of formula 1(b) with an alkylating reagent such as $R^2$-W, wherein $R^{12}$ is as described above, in appropriate conditions, such as in a dipolar aprotic solvent, such as DMF, in the presence of a base, such as sodium hydride. W is a suitable leaving group, such as a halo group or a sulfonyl group.

Scheme 5

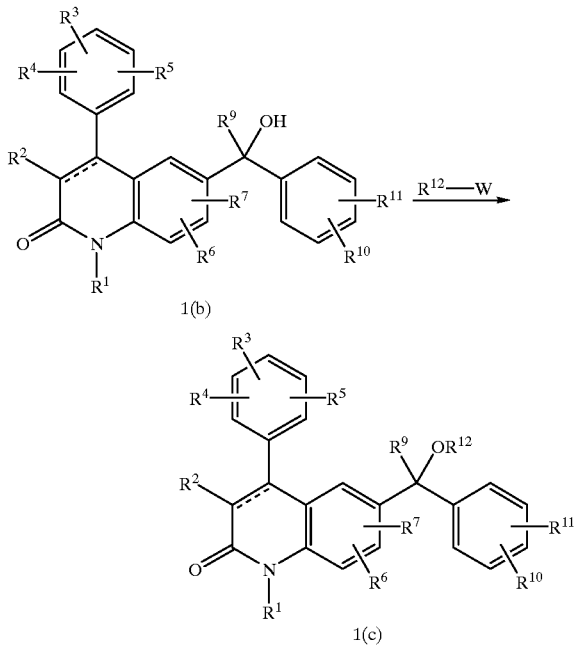

As an alternative to the above reaction procedure, compounds of formula 1(c) may also be prepared by reacting a compound of formula 1(b) with a reagent of formula $R^{12}$—OH, wherein $R^{12}$ is as described above, in acidic medium.

Compounds of formula 1(b) may also be converted into compounds of formula 1(g), wherein $R^{12}$ is hydrogen and $R^{13}$ is replaced with $C_1$–$C_6$ alkylcarbonyl, by reacting compounds of formula 1(b) in acidic medium, such as sulfuric acid, with $C_1$–$C_6$ alkyl-CN in a Ritter-type reaction. Further, compounds of formula 1(b) may also be converted into compounds of formula 1(g), wherein $R^{12}$ and $R^{13}$ are hydrogen, by reacting a compound of formula 1(b) with ammonium acetate and subsequent treatment with $NH_3$(aq.).

With reference to Scheme 6 below, compounds of formula 1(b), referred to above, may also be converted into compounds of formula 1(d), wherein $R^8$ is hydrogen, by submitting a compound of formula 1(b) to appropriate reducing conditions, such as stirring in trifluoroacetic acid in the presence of an appropriate reducing agent, such as sodium borohydride, or, alternatively, stirring the compound of formula 1(b) in acetic acid in the presence of formamide. Further, the compound of formula 1(d) wherein $R^8$ is hydrogen may be converted into a compound of formula 1(e) wherein $R^{12}$ is $C_1$–$C_{10}$ alkyl by reacting the compound of formula 1(d) with a reagent of formula 5, wherein W is an appropriate leaving group, in an appropriate solvent, such as diglyme, in the presence of a base, such as potassium tert-butoxide.

Scheme 6

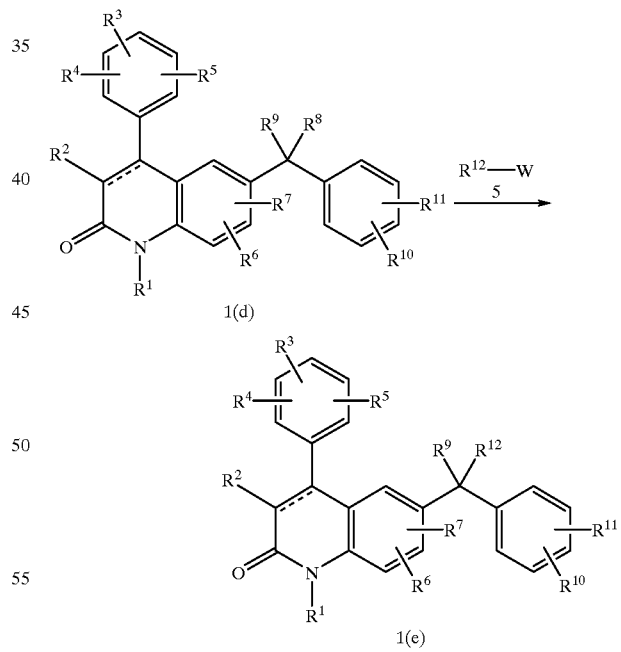

With reference to Scheme 7 below, compounds of formula 1 may be prepared by reacting a nitrone of formula 6 with the anhydride of a carboxylic acid, such as acetic anhydride, thus forming the corresponding ester on the 2-position of the quinoline moiety. Said quinoline ester can be hydrolyzed in situ to the corresponding quinolinone using a base, such as potassium carbonate.

Scheme 7

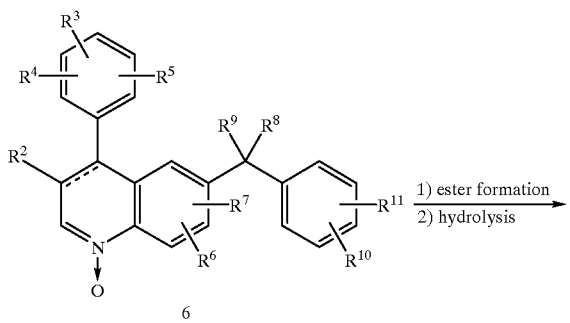

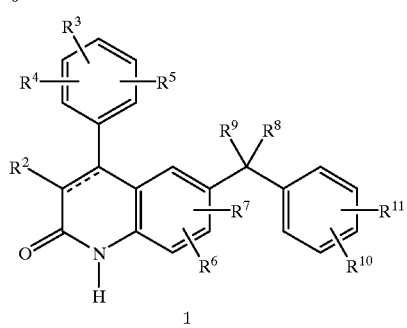

Alternatively, compounds of formula I can be prepared by reacting a nitrone of formula 6 with a sulfonyl containing electrophilic reagent, such as p-toluenesulfonylchloride, in the presence of a base, such as aqueous potassium carbonate. The reaction initially involves the formation of a 2-hydroxyquinoline derivative which is subsequently tautomerized to the desired quinolinone derivative. The application of conditions of phase transfer catalysis, which are familiar to those skilled in the art, may enhance the rate of the reaction.

Compounds of formula 1 may also be prepared by an intramolecular photochemical rearrangement of compounds of formula 6, referred to above. Said rearrangement can be carried out by dissolving the reagents in a reaction-inert solvent and irradiating at a wavelength of 366 nm. It is advantageous to use degassed solutions and to conduct the reaction under an inert atmosphere, such as oxygen-free argon or nitrogen gas, in order to minimize undesired side reactions or reduction of quantum yield.

The substituents of the compounds of formula 1 may be converted to other substituents falling within the scope of formula 1 via reactions or functional group transformations familiar to those skilled in the art. A number of such transformations are already described above. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl moieties may be replaced by hydrogen by diazotation reactions familiar to those skilled in the art, and subsequent replacement of the diazo-group by hydrogen; alcohols may be converted into esters and ethers; primary amines may be converted into secondary or tertiary amines; double bonds may be hydrogenated to the corresponding single bond.

With reference to Scheme 8 below, intermediates of formula 3, referred to above, may be prepared by reacting a quinolinone derivative of formula 8 with an intermediate of formula 9, or a functional derivative thereof, under appropriate conditions, such as in the presence of a strong acid (for example, polyphosphoric acid) in an appropriate solvent. The intermediate of formula 8 may be formed by cyclization of an intermediate of formula 7 by stirring in the presence of a strong acid, such as polyphosphoric acid. Optionally, said cyclization reaction may be followed by an oxidation step, which can be performed by stirring the intermediate formed after cyclization in an appropriate solvent, such as a halogenated aromatic solvent (for example, bromobenzene), in the presence of an oxidizing agent, such as bromine or iodine. At this stage, the $R^1$ substituent may be changed to a different moiety by a functional group transformation reaction familiar to those skilled in the art.

Scheme 8

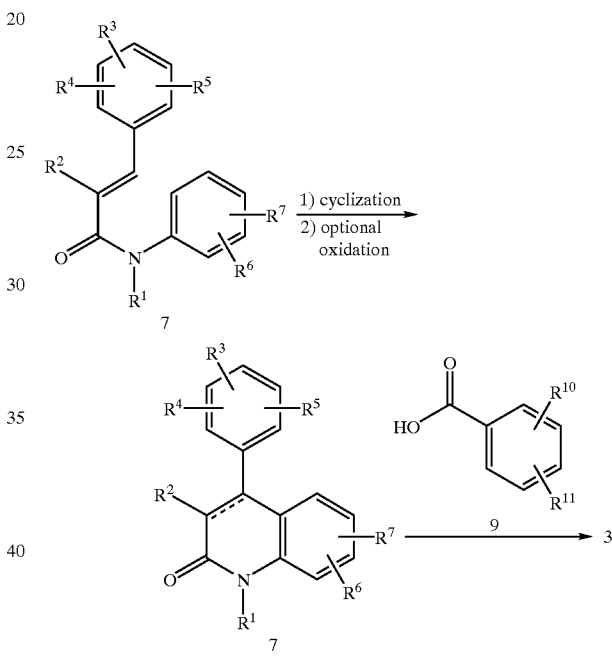

With reference to Scheme 9 below, intermediates of formula 3(a-1), which are intermediates of formula 3 wherein the dotted line is a bond and $R^1$ and $R^2$ are hydrogen, can be prepared starting from an intermediate of formula 17, which is conveniently prepared by protecting the corresponding ketone. Said intermediate of formula 17 is stirred with an intermediate of formula 18 in the presence of a base, such as sodium hydroxide, in an appropriate solvent, such as an alcohol (for example, methanol). The resulting intermediate of formula 16 will undergo hydrolysis of the ketal and ring opening of the isoxazole moiety by stirring the intermediate of formula 16 with an acid, such as $TiCl_3$, in the presence of water. Subsequently, acetic anhydride can be used to prepare an intermediate of formula 15, which will undergo ring closure in the presence of a base, such as potassium tert-butoxide.

Intermediates of formula 3(a-1) can be converted to intermediates of formula 3(a), which are intermediates of formula 3 wherein the dotted line represents a bond, $R^2$ is hydrogen, and $R^1$ is other than hydrogen as defined above, using N-alkylation procedures familiar to those skilled in the art.

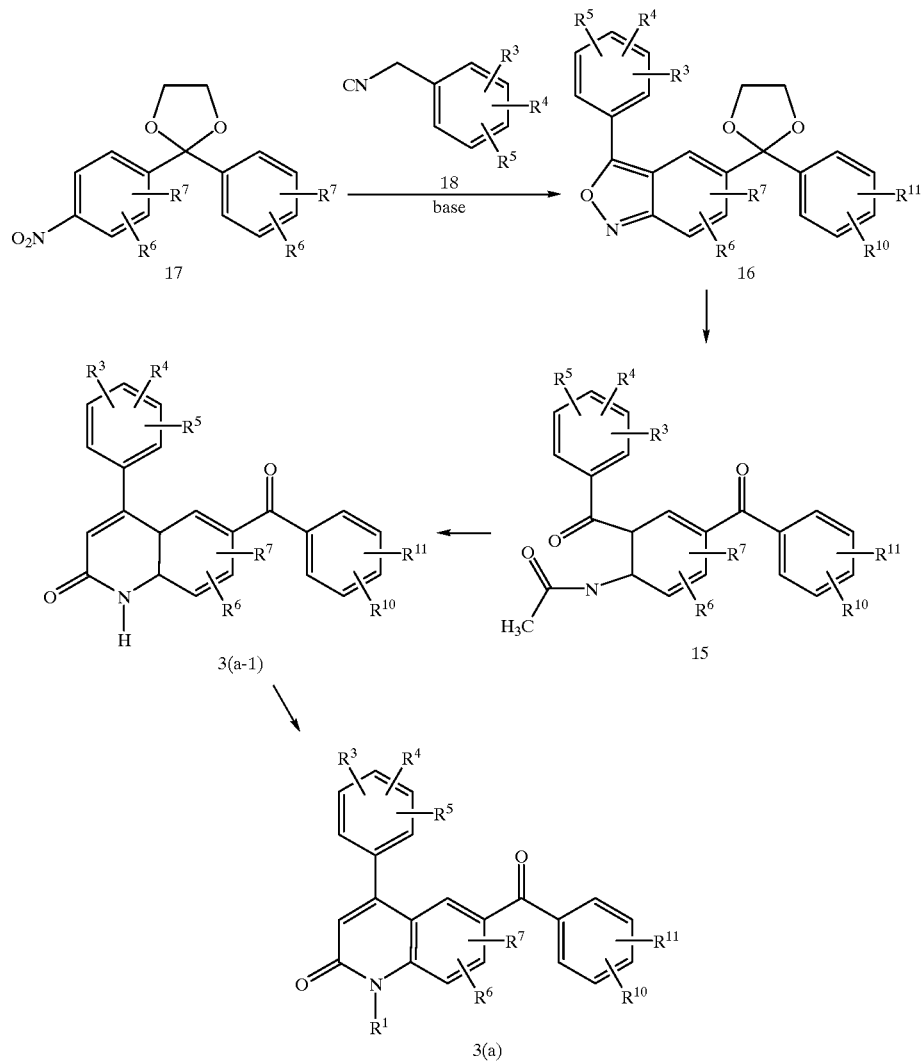

With reference to Scheme 10 below, an alternative method of preparing intermediates of formula 3(a-1), wherein $R^1$ is hydrogen, begins with an intermediate of formula 16 which can be converted to an intermediate of formula 19 using catalytic hydrogenation conditions, such as by using hydrogen gas and palladium on carbon in a reaction-inert, solvent such as tetrahydrofuran (THF). The intermediates of formula 19 can be converted into an intermediate of formula 20 by submitting the intermediate of formula 19 to an acetylation reaction, such as by treatment with the anhydride of a carboxylic acid (for example, acetic anhydride) in a reaction-inert solvent, such as toluene, and subsequent treatment with a base, such as potassium tert-butoxide, in a reaction-inert solvent, such as 1,2-dimethoxyethane. The intermediate of formula 3(a-1) can be obtained by subjecting the intermediate of formula 20 to acidic conditions.

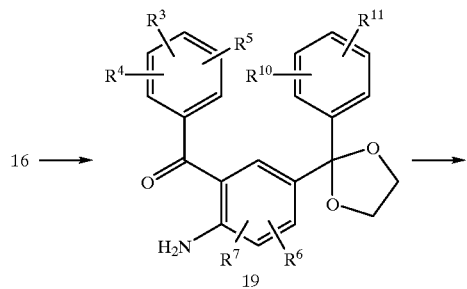

-continued

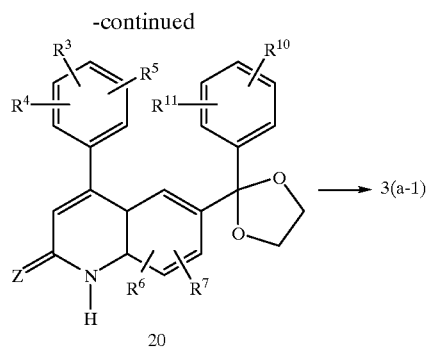

With reference to Scheme 11 below, the intermediate of formula 2, referred to above, may be prepared by reacting an intermediate of formula 10, wherein W is an appropriate leaving group, such as halo, with an intermediate ketone of formula 11. This reaction is done by converting the intermediate of formula 10 into a organometallic compound, by stirring it with a strong base such as butyl lithium, and subsequently adding the intermediate ketone of formula 11. Although this reaction gives at first instance a hydroxy derivative ($R^8$ is hydroxy), said hydroxy derivative can be converted into other intermediates wherein $R^8$ has another definition by performing functional group transformations familiar to those skilled in the art.

Scheme 11

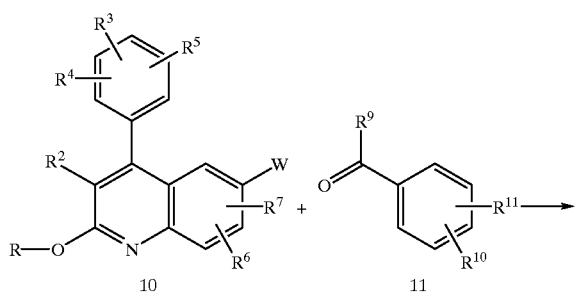

With reference to Scheme 12 below, the intermediate nitrones of formula 6 can be prepared by N-oxidizing a quinoline derivative of formula 12 with an appropriate oxidizing agent, such as m-chloro-peroxybenzoic acid or $H_2O_2$, in an appropriate solvent, such as dichloromethane.

Scheme 12

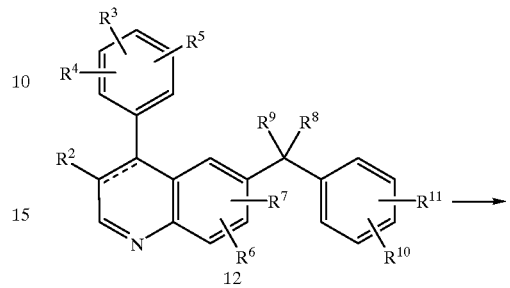

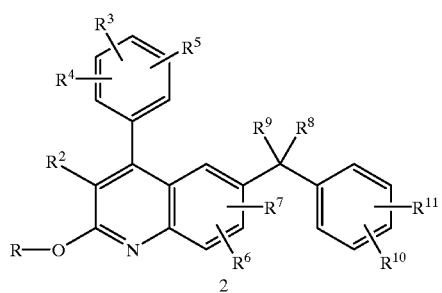

Said N-oxidation may also be carried out on a precursor of a quinoline of formula 12.

The intermediate of formula 12 may be metabolized in vivo into compounds of formula 1 via intermediates of formula 6. Hence, intermediates of formula 12 and 6 may act as prodrugs of compounds of formula 1. Such prodrugs are within the scope of the present invention.

With reference to Scheme 13 below, the compound of formula 24, wherein Y is bromo, iodo or trifluoromethanesulfonyloxy, can be reacted to add an $R^3$, $R^4$ or $R^5$ group (addition of $R^3$ is illustrated) of the formula —C≡$CR^{16}$, in particular a terminal alkyne such as (trimethylsilyl)acetylene, using palladium catalysis (with a palladium reagent, such as bis(triphenylphosphine)-palladium(II) chloride) in the presence of copper (I) salts, such as copper (I) iodide, in an amine solvent, such as diethylamine, at a temperature ranging from 0°C. to 100° C. to give a compound of formula 28 wherein $R^3$ is an alkyne as described above. Co-solvents, such as (N,N-dimethylformamide) DMF, may be added to help solubilize the reactants. Additional methods of effecting such an alkyne addition are referred to in U.S. Pat. No. 5,747,498.

Scheme 13

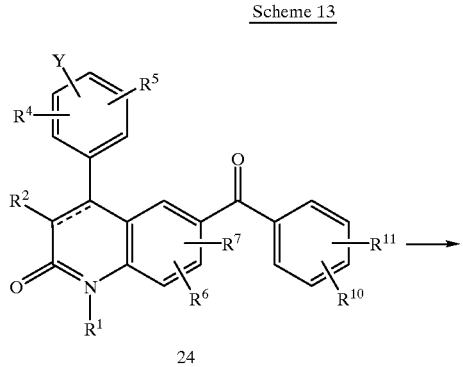
24

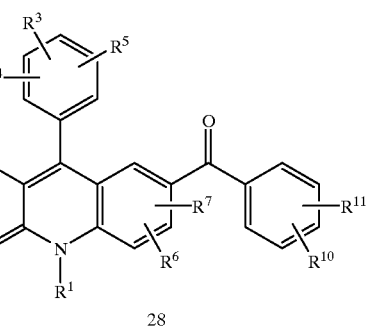
28

With reference to Scheme 14 below, the compound of formula 26 can be prepared by reacting a compound of formula 25 with an intermediate of formula 27 where $R^{12}$ is H or phenyl. This reaction requires the presence of a suitable base, such as tert-butyl lithium (when $R^{12}$=H) or lithium 2,2,6,6,-tetramethylpiperidine (when $R^{12}$=phenyl), in an appropriate solvent, such as THF. The —$SR^{12}$ group can be reductively removed from the compound of formula 26 with RANEY™ nickel or oxidatively with nitric acid or aqueous hydrogen peroxide in acetic acid.

Scheme 14

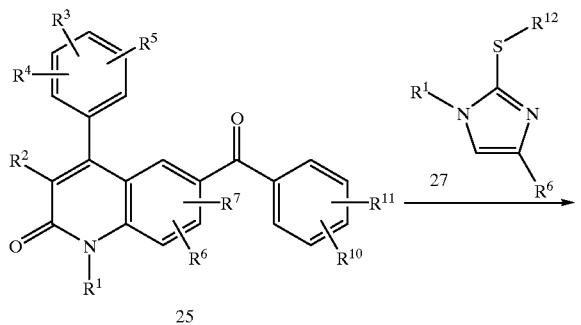

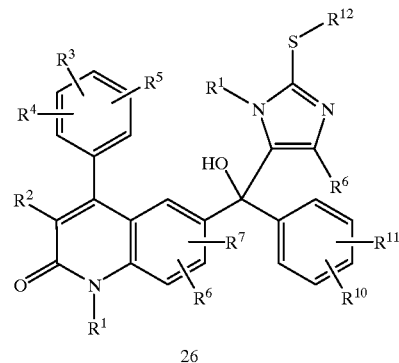
26

The compounds of formula 1 and some of the intermediates described above may have one or more stereogenic centers in their structure. Such stereogenic centers may be present in a R or a S configuration. Oxime moieties, such as where $R^3$, $R^4$, $R^5$, $R^6$ or $R^7$ is —CH=NOR$^{12}$, may exist in E or Z configurations.

The compounds of formula 1 as prepared in the above processes are generally racemic mixtures of enantiomers which can be separated from one another following resolution procedures familiar to those skilled in the art. The racemic compounds of formula 1 may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula 1 involves liquid chromatography using a chiral stationary phase. Said pure stereochemically isomeric forms may also be derived from the corresponding pure stereochemically isomeric forms of the appropriate starting materials, provided that the reaction occurs sterospecifically. Preferably if a specific stereoisomer is desired, said compound will be synthesized by stereospecfic methods of preparation. These methods will advantageously employ enantiomerically pure starting materials.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula 1 are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

The compounds of formula 1 and their pharmaceutically acceptable salts and solvates (hereinafter referred to, collectively, as "the therapeutic compounds") can be administered orally, transdermally (e.g., through the use of a patch), parenterally or topically. Oral administration is preferred. In general, compounds of the formula 1 and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula 1 exhibit activity as Ras farnesylation inhibitors and are useful in the treatment of cancer and the inhibition of abnormal cell growth in mammals, including humans. The activity of the compounds of formula 1 as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/$MgCl_2$/EDTA buffer (using a Dounce homogenizer; 10–15 strokes), centrifuging the homogenates at 1000 grams for 10 minutes at 4 G, re-centrifuging the supernatant at 17,000 grams for 15 minutes at 4 G, and then collecting the resulting supernatant. This supernatant is diluted to contain a final concentration of 50 mM Tris HCl (pH 7.5), 5 mN DTT, 0.2 M KCl, 20 mM $ZnCl_2$, 1 mM PMSF and re-centrifuged at 178,000 grams for 90 minutes at 4 G. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H)

Scintillation Proximity Assay (SPA) kit (TRKQ 7010). FTase enzyme activity is determined in a volume of 100 ml containing 50 mM N-(2-hydroxy ethyl) piperazine-N2-ethane sulfonic acid) (HEPES), pH 7.5, 30 mM $MgCl_2$, 20 uM KCl, 5 mM $Na_2HPO_4$, 5 mM dithiothreitol (DTT), 0.01% Triton X-100, 5% dimethyl sulfoxide (DMSO), 20 mg of crude FTase, 0.12 mM [3H]-farnesyl pyrophosphate ([3H]-FPP; 36000 dpm/pmole, Amersham LifeScience), and 0.2 mM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 ml of steptavidin-coated SPA beads (TRKQ 7010) per well and incubating the reaction mixture for 30 minutes at room temperature. The amount of radio-activity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% dimethyl sulfoxide (DMSO). Inhibition of farnesyl transferase activity is determined by calculating percent incorporation of tritiated-farnesyl in the presence of the test compound vs. its incorporation in control wells (absence of inhibitor). ICso values, that is, the concentration required to produce half maximal farnesylation of Bt-KTKCVIS, is determined from the dose-responses obtained.

The following Examples further illustrate the invention. In the following Examples, "Et" refers to ethyl, "Me" refers to methyl, and "Ac" refers to acetyl.

EXAMPLE 1

6-[(4-Chloro-phenyl)-hydroxy-(3-methyl-3H-imidazol-4-yl)-methyl]-1-methyl-4-(3-trimethylsilanylethynyl-phenyl)-1H-quinolin-2-one 1A. 5-[2-(4-Chloro-phenyl)-[1,3]dioxolan-2-yl]-3-(3-iodo-phenyl)-benzo[c]isoxazole 2-(4-Chlorophenyl)-2-(4-nitrophenyl)-1,3dioxolane (38.7 g, 127 mMol) was suspended in 190 mL of methanol (MeOH) under an atmosphere of dry $N_2$. To this solution was added (3-iodophenyl)acetonitrile (46.3 g, 190 mMol) and 25.4 g (625 mMol) of sodium hydroxide (NaOH). The solution was then heated to reflux and reacted at this temperature for 2 hours. The reaction mixture was cooled to ambient temperature and the MeOH was removed under vacuum. The resulting red oil was partitioned between dichloromethane (DCM) and 0.1 N aqueous NaOH. The DCM layer was washed successively with 0.1 N aqueous NaOH and then brine. The DCM layer was dried over $MgSO_4$, filtered and concentrated under vacuum to give a dark red oil. The oil was stirred in MeOH and the titled compound precipitated out as a yellow solid. The yellow solid was washed with MeOH and dried under vacuum to give 52.4 g of the titled compound which was used without further purification.

1B. [6-Amino-3-(4chloro-benzoyl)cychlohexa-2,4dienyl]-(3-iodo-phenyl)-methanone

5-[2-(4-Chloro-phenyl)-[1,3]dioxolan-2-yl]-3-(3-iodo-phenyl)-benzo[c]isoxazole (65.4 g 130 mMol) was dissolved in a solution of tetrahydrofuran (THF) (500 mL) and DCM (100 mL). To this solution, was added 500 mL of titanium(III) chloride (10 wt. % solution in 20–30 wt. % hydrochloric acid (HCl)) and the reaction mixture was stirred for 1 hour. An additional 100 mL of titanium(III) chloride (10 wt. % solution in 20–30 wt. % HCl was added to the reaction mixture and the reaction mixture was stirred for 2.5 hours. The reaction mixture was then poured into ice water and the resulting heterogeneous solution was extracted with DCM. The DCM layer was successively washed with aqueous saturated $NaHCO_3$ and brine. The DCM layer was dried over $MgSO_4$, filtered and concentrated under vacuum to give titled compound as an orange oil (60 g). The oil was used without further purification.

1C. 6-(4-Chloro-benzoyl)-4-(3-iodo-phenyl)-1H-quinolin-2-one

[6-Amino-3-(4-chloro-benzoyl)-cyclohexa-2,4-dienyl]-(3-iodo-phenyl)-methan-one (60 g, 130 mMol) was dissolved in anhydrous toluene (450 mL) under an atmosphere of dry $N_2$. To this solution was added 180 mL of triethylamine ($NEt_3$), 50 mL of acetic anhydride ($AC_2O$) and 1.60 g (13.0 mMol) of 4-dimethylaminopyridine (DMAP). The reaction mixture was then heated to reflux and stirred at this temperature for 20 hours. The reaction mixture was cooled to ambient temperature and the precipitate was collected via suction filtration. The solid was washed with ethyl ether ($Et_2O$) and dried under vacuum to give of the titled compound (63 g) which was used without further purification.

1D. 6-(4-Chloro-benzoyl)-4-(3-iodo-phenyl)-1-methyl-1H-quinolin-2-one 6-(4-Chloro-benzoyl)-4-(3-iodo-phenyl)-1H-quinolin-2-one (63 g, 130 mMol) was dissolved in THF (500 mL) under an atmosphere of dry $N_2$. To this solution, was added a 10 N aqueous NaOH (550 mL), benzyltriethylammonium chloride (13.8 g, 60.5 mMol) and methyl iodide (13.5 mL, 212.0 mMol). The reaction mixture was stirred at ambient temperature for 15 hours after which time it was partitioned between DCM and water. The DCM layer was successively washed with water (4 times) and then brine. The organic layer was dried over $MgSO_4$, filtered and concentrated under vacuum to give 51.2 g of a yellow solid as the titled compound which was used without further purification.

1E. 6-(4-Chloro-benzoyl)-1-methyl-4-(3-trimethylsilanylethynyl-phenyl)-1H-quinolin-2-one 6-(4-Chloro-benzoyl)-4-(3-iodo-phenyl)-1-methyl-1H-quinolin-2-one (9.98 g, 20.0 mMol) was suspended in diethylamine (300 mL). To this solution was added 50 mL of anhydrous N,N-dimethylformamide (DMF), (trimethylsilyl)acetylene (8.5 mL) and bis (triphenylphosphine)-palladium(II) chloride (1.40 g, 2.00 mMol). The flask was covered with aluminum foil and then copper(I) iodide (780 mg, 4.09 mMol) was added causing the reaction mixture to exotherm. After stirring overnight under an atmosphere of dry $N_2$ at ambient temperature, the reaction mixture was concentrated under vacuum and the residue was chromatographed on flash silica gel eluting with a gradient of DCM to MeOH/DCM (2:98) to give 8.55 g of the titled product as a solid.

1F. 6-[(4-Chloro-phenyl)-hydroxy-(2-mercapto-3-methyl-3H-imidazol-4-yl]-1-methyl-4-(3-trimethylsilanylethynyl-phenyl)-1H-quinolin-2-one 2-Mercapto-1-methylimidazole (2.08 g, 18.2 mMol) was dissolved in anhydrous THF (200 mL) under an atmosphere of dry $N_2$. The solution was cooled to −78° C. and a solution of tert-butyl lithium (1.7 M in pentane, 22 mL, 37 mMol) was added. The solution was then warmed to 0° C. After a yellow precipitate formed, the solution was cooled to −78° C. and a solution of 6-(4chloro-benzoyl)-1-methyl-4-(3-trimethylsilanyl ethynyl-phenyl)-1H-quinolin-2-one (8.55 g, 18.2 mMol) in anhydrous THF (25 mL) was added. After 30 minutes, the solution was warmed to 0° C. and stirred at this temperature for 1 hour. The reaction mixture was then warmed to ambient temperature and stirred overnight. The reaction was quenched with 20 mL of saturated aqueous ammonium chloride ($NH_4Cl$) and then partitioned between DCM and water. The DCM layer was dried over sodium sulfate ($Na_2SO_4$), filtered and concentrated under vacuum. The residue was chromatographed on flash silica gel eluting with a gradient from DCM to MeOH/DCM (3:97) to give 5.0 g of the titled compound as a solid.

1G. 6-[(4-Chloro-phenyl)-hydroxy-(3-methyl-3H-imidazol-4-yl)-methyl]-1-methyl-4-(3-trimethylsilanylethynyl-phenyl)-1H-quinolin-2-one 6-[(4-Chloro-phenyl)-hydroxy-(2-mercapto-3-methyl-3H-imidazol-4-yl)-methyl]-1-methyl-4-(3-trimethylsilanylethynyl-phenyl)-1H-quinolin-2-one (5.0 g, 8.6 mMol) was dissolved in ethanol (40 mL) to which was added Raney™ nickel (ca. 10 g) and the reaction was heated to reflux. More RANEY™ nickel was added every 20 minutes until mass spectral analysis of the reaction showed that the starting material had been consumed. The reaction mixture was cooled to ambient temperature and filtered through CELITE™ (diatomaceous earth). The CELITE™ was washed with copious amounts of ethanol. The filtrates were combined and concentrated under vacuum to give 3.88 g of the titled compound.

C.I. m/z 552 [M+1]; $^1$H NMR ($CD_3OD$) δ7.64–7.75 (m, 3H), 7.17–7.48 (m, 9H), 6.59 (s, 1 H), 6.17 (s, 1H), 3.79 (s, 3H), 3.42 (s, 3H), 0.23 (s, 9H).

EXAMPLE 2

6-[(4-Chloro-phenyl)-hydroxy-(3-methyl-3H-imidazol-4-1)-methyl]-4-(3-ethynyl-phenyl)-1-methyl-1H-quinolin-2-one 6-[(4-Chloro-phenyl)-hydroxy-(3-methyl-3H-imidazol-4-yl)-methyl]-1-methyl-4-(3-trimethylsilanylethynyl-phenyl)-1H-quinolin-2-one (3.88 9, 7.03 mMol) was dissolved in THF (10 mL) under an atmosphere of dry $N_2$. To this solution was added a solution of 1.0 N tetrabutylammonium fluoride in THF (20 mL, 20 mMol). The reaction mixture was stirred overnight at ambient temperature and was then concentrated under vacuum. The residue was partitioned between 4-(dicyanomethylene)-2-methyl-(4-dimethylamino-styryl)-4H-pyran (DCM) and water. The DCM layer was saved and washed 3 more times with water and then with brine. The DCM layer was dried over $Na_2SO_4$, filtered and concentrated under vacuum. The residue was chromatographed on flash silica gel eluting with a gradient from DCM to MeOH/DCM (4:96) to give 3.01 g of the titled compound.

C.I. m/z 480 [M+1]; $^1$H NMR ($CD_3OD$) δ7.75 (dd, J=2.1, 8.9 Hz, 1H), 7.69 (s, 1H), 7.66 (d, 8.5 Hz, 1H), 7.52 (d, J=7.9 Hz, 1H), 7.41 (t, J=7.7 Hz, 1H), 7.38 (s, 1H), 7.29 (m, 3H), 7.23 (d, J=1.7 Hz, 1H), 7.17 (d, J=8.5 Hz, 2H), 6.59 (s, 1H), 6.16 (s,1H), 7.29 (m, H), 3.60 (s, 1H), 3.42 (s, 3H).

Separation of the Enantiomers of 6-[(4-Chloro-phenyl)-hydroxy-(3-methyl-3H-imidazol-4-yl)-methyl]-4-(3-ethynyl-phenyl)-1-methyl-1H-qinolin-2-one 6-[(4-Chloro-phenyl)-hydroxy-(3-methyl-3H-imidazol-4-yl)-methyl]-4-(3-ethynyl-phenyl)-1-methyl-1H-quinolin-2-one (4.96 g) was separated into its enantiomers and purified by high-performance liquid chromatography over CHIRAL-PAK™ AD (manufactured by Daicel Chemical Industries, LTD, Osaka, Japan) (20 μm; eluent: Hexane/isopropanol/diethylamine 85/15/0.1; 30° C.). Under these conditions, 1.73 g of the faster eluting enantiomer A ($\{\alpha\}_D^{20}$=−25.1 (c=50.0 mg/5 mL)) was obtained and 2.07 g of the slower moving enantiomer B ($\{\alpha\}_D^{20}$=+24.2 (c=27.7 mg/5 mL)). Both enantiomers were >97% optically pure.

EXAMPLE 3

6-[Amino-(4-chloro-phenyl)-(3-methyl-3H-imidazol-4-yl)-methyl]-4-(3-ethynyl-phenyl)-1-methyl-1H-quinolin-2-one 6-[(4-Chloro-phenyl)-hydroxy-(3-methyl-3H-imidazol-4-yl)-methyl]-4-(3-ethynyl-phenyl)-1-methyl-1H-quinolin-2-one (1.75 mg, 3.65 mMol) was dissolved in 5.0 mL of thionyl chloride ($SOCl_2$) and stirred at room temperature under an atmosphere of dry $N_2$ for 2 hours. The reaction mixture was then concentrated under reduced pressure and the resulting solid was taken up in toluene and concentrated under vacuum. The resulting solid was dissolved in THF (15 mL) and to this mixture was added concentrated ammonium hydroxide (20 mL). The reaction mixture was stirred at ambient temperature for 1 hour and was then partitioned between DCM and 1.0 N aqueous NaOH. The aqueous layer was extracted again with DCM and the organic layers were then combined, dried over $Na_2SO_4$, filtered and concentrated under vacuum to give a brown solid. The residue was chromatographed on flash silica gel eluting with a gradient from MeOH/ethyl acetate (EtOAc)/ammonium hydroxide ($NH_4OH$) (5:95:0.1) to MeOH/EtOAc/$NH_4OH$ (10:90:0.1) to give 643 mg of the titled compound.

C.I. m/z 479 [M+1]; $^1$H NMR ($CD_3OD$) δ7.84 (dd, J=2.3, 9.1 Hz, 1H), 7.70 (d, 8.9 Hz, 1H), 7.57 (s, 1H), 7.51 (m, 1H), 7.37 (t, J=7.7 Hz, 1H), 7.33 (s, 1H), 7.28 (m, 2H), 7.21 (dd, J=1.0, 7.7 Hz, 1H), 7.10 (d, J=8.5 Hz, 2H), 6.96 (d, J=1.3 Hz, 1H), 6.57 (s, 1H), 6.10 (s, 1H), 3.78 (s, 3H), 3.60 (s, 1H), 3.41 (s, 3H).

Separation of the Enantiomers of 6-[Amino-(4-chloro-phenyl)-(3-methyl-3H-imidazol-4-yl)-methyl]-4-(3-ethynyl-phenyl)-1-methyl-1-H-quinolin-2-one 6-[Amino-(4chloro-phenyl)-(3-methyl-3H-imidazol-4-yl)-methyl]-4-(3-ethynyl-phenyl)-1-methyl-1H-quinolin-2-one (5.25 g) was separated into its enantiomers and purified by high-performance liquid chromatography over CHIRAL- CEL™ OD (manufactured by Daicel Chemical Industries, LTD, Osaka, Japan) (20 µm; eluent: Hexane/isopropanol/diethylamine 67/33/0.1; 25° C.). Under these conditions, 2.29 g of the faster eluting enantiomer A was obtained and 1.60 g of the slower moving enantiomer B. Both enantiomers were >97% optically pure.

EXAMPLE 4

6-[(4-Chloro-phenyl)-hydroxy-(3-methyl-3H-imidazol-4-yl)-methyl]-1-methyl-4-[3-(3-methyl-but-1-ynyl)-phenyl]-1H-quinolin-2-one The same procedure was used as described in example 1 except that 3-methyl-1-butyne was used in the place of (trimethylsilyl)acetylene in step 1E to give the titled compound.

C.I. m/z 522 [M+1]; $^1$H NMR (CDCl$_3$) δ7.60 (m, 2H), 7.42 (d, J=7.9 Hz, 1H), 7.37 (d, J=7.9 Hz, 1H), 7.25–7.29 (m, 5H), 7.17 (d, J=8.7 Hz, 2H), 7.03 (d, J=8.1 Hz, 1H), 6.60 (s, 1H), 6.31 (brs, 1H), 3.70 (s, 3H), 3.43 (s, 3H), 2.79 (m, J=6.9 Hz, 1H), 1.26 (d, J=6.9 Hz, 6H).

EXAMPLE 5

6-[(4-Chloro-phenyl)-hydroxy-(3-methyl-3H-imidazol-4-yl)-methyl]-4-[3-(3,3-dimethyl-but-1-ynyl)-phenyl]-1-methyl-1H-quinolin-2-one The same procedure was used as described in example 1 except that 3,3-dimethyl-1-butyne was used in the place of (trimethylsilyl)acetylene in step 1E to give the titled compound.

C.I. m/z 536 [M+1]; $^1$H NMR (CDCl$_3$) δ7.84 (brs, 1H), 7.40 (m, 3H), 7.21–7.27 (m, 4H), 7.15 (d, J=8.5 Hz, 2H), 7.02 (d, J=7.3 Hz, 1H), 6.61 (s, 1H), 6.34 (brs, 1H), 3.70 (s, 3H), 3.48 (s, 3H), 1.30 (s, 9H).

EXAMPLE 6

6-[(4-Chloro-phenyl)-hydroxy-(3-methyl-3H-imidazol-4-yl)-methyl]-1-methyl-4-[3-(4-methyl-pent-1-ynyl)-phenyl]-1H-quinolin-2-one The same procedure was used as described in example 1 except that 4-methyl-1-pentyne was used in the place of (trimethylsilyl)acetylene in step 1E to give the titled compound.

C.I. m/z 536 [M+1]; $^1$H NMR (CDCl$_3$) δ7.84 (brs, 1H), 7.62 (d, J=8.1 Hz, 1H), 7.39–7.44 (m, 2H), 7.25–7.30 (m, 5H), 7.17 (d, J=8.3 Hz, 2H), 7.05 (d, J=7.2 Hz, 1H), 6.63 (s, 1H), 6.36 (brs, 1H), 3.72 (s, 3H), 3.49 (s, 3H), 2.31 (d, J=6.4 Hz, 2H), 1.91 (m, 1H), 1.03 (d, J=6.6 Hz, 6H).

EXAMPLE 7

6-[(4-Chloro-phenyl)-(3-methyl-3H-imidazol-4-yl)-[1,2,4]triazol-1-yl-methyl]-4-[3-(3,3-dimethyl-but-1-ynyl)-phenyl]-1-methyl-1H-quinolin-2-one 6-[(4chloro-phenyl)-hydroxy-(3-methyl-3H-imidazol-4-yl)-methyl]-4-[3-(3,3-dimethyl-but-1-ynyl)-phenyl]-1-methyl-1H-quinolin-2-one (330 mg, 0.633 mMol) was dissolved in 4 mL of thionyl chloride and stirred at ambient temperature under a stream of dry N$_2$ for 2 hours. The reaction mixture was then concentrated under vacuum and toluene (5 mL) was added to the reaction mixture which was subsequently concentrated under vacuum to give a yellow solid. 210 mg of the yellow solid was dissolved in 5.0 mL of anhydrous DMF under an atmosphere of dry N$_2$. To this solution was added 800 mg of potassium carbonate and 300 mg of 1,2,4-triazole and the reaction mixture was subsequently heated to 80° C. and stirred overnight at this temperature. The reaction mixture was then concentrated under vacuum and partitioned between EtOAc and water. The EtOAc layer was washed 3 more times with water and then with brine. The EtOAc layer was then dried over Na$_2$SO$_4$, filtered and concentrated under vacuum to give a yellow solid. The solid was chromatographed on flash silica gel eluting with a gradient of MeOH/DCM/NH$_4$OH (2/98/0.1) to MeOH/DCM/NH$_4$OH (7/93/0.1) to give 150 mg of the titled product as a white solid.

$^1$H NMR (CDCl$_3$) δ8.06 (s, 1H), 7.89 (s, 1H), 7.59 (brs, 1H), 7.41 (d, J=8.7 Hz, 2H), 1H), 7.22–7.27 (m, 5H), 7.00–7.05 (m, 2H), 6.89 (d, J=8.7 Hz, 2H), 6.67 (s, 1H), 6.54 (brs, 1H), 3.75 (s, 3H), 3.08 (s, 3H), 1.31 (s, 9H).

EXAMPLE 8

6-[(4-Chloro-phenyl)-(3-methyl-3H-imidazol-4-yl)-[1,2,4]triazol-1-yl-methyl]-1-methyl-4-[3-(3-methyl-but-1-ynyl)-phenyl]-1H-quinolin-2-one The same procedure was used as described in example 7 except that 6-[(4-chloro-phenyl)-hydroxy-(3-methyl-3H-imidazol-4-yl)-methyl]-1-methyl-4-[3-(3-methyl-but-1-ynyl)-phenyl]-1H-quinolin-2-one was used in the place of 6-[(4-chloro-phenyl)-hydroxy-(3-methyl-3H-imidazol-4-yl)-methyl]-4-[3-(3,3-dimethyl-but-1-ynyl)-phenyl]-1-methyl-1H-quinolin-2-one to give the titled compound.

$^1$H NMR (CDCl$_3$) δ8.06 (s, 1H), 7.90 (s, 1H), 7.43–7.48 (m, 2H), 7.20–7.34 (m, 6H), 7.01 (d, J=8.1 Hz, 1H), 6.98 (s, 1H), 6.79 (m, 3H), 6.70 (s, 1H), 3.77 (s, 3H), 2.80 (m, 1H), 1.26 (d, J=6.9 Hz, 6H).

EXAMPLE 9

6-[(4-Chloro-phenyl)-hydroxy-(3-methyl-3H-imidazol-4-yl)-methyl]-4-(3-ethynyl-4-fluoro-phenyl)-1-methyl-1H-quinolin-2-one 9A. 4-Bromomethyl-1-fluoro-2-iodo-benzene 4-Fluoro-3-iodotoluene (50 g, 210 mMol), N-bromosuccinimide (37.7 g, 212 mMol) and 2,2'-azobis-(2-methylpropionitrile) (348 mg, 2.12 mMol) were dissolved in carbon tetrachloride (300 mL) under an atmosphere of dry N$_2$. The mixture was heated to reflux for 4 hours and then cooled to ambient temperature. The mixture was concentrated under vacuum and triturated with Et$_2$O. The filtrate was successively washed with water, aqueous saturated NaHCO$_3$ and brine. The ether layer was dried over MgSO$_4$, filtered and concentrated under vacuum to give a red oil. The oil was chromatographed on flash silica gel eluting with hexanes to give 33.8 g of the titled compound as a white solid.

9B. (4-Fluoro-3-iodo-phenyl)-acetonitrile

4-Bromomethyl-1-fluoro-2-iodo-benzene (33.8 g, 107 mMol) was added to 240 mL of a 0.5 M solution of lithium cyanide in DMF. The reaction mixture was heated to 80° C.

under an atmosphere of dry $N_2$ and stirred overnight at this temperature. The mixture was then cooled to ambient temperature and partitioned between $Et_2O$ and 0.1 N aqueous NaOH. The $Et_2O$ layer was then washed 4 more times with 0.1 N aqueous NaOH. The $Et_2O$ layer was then dried over $MgSO_4$, filtered and concentrated under vacuum to give 24.7 9 of the titled compound as a red solid which was used without purification.

9C. 6-[(4-chloro-phenyl)-hydroxy-(3-methyl-3H-imidazol-4-yl)-methyl]-4-(3-ethynyl-4-fluoro-phenyl)-1-methyl-1H-quinolin-2-one The procedure was used as that of examples 1 and 2 except that (4-fluoro-3-iodophenyl)acetonitrile was used in the place of (3-iodophenyl)acetonitrile in step 1A to give the titled compound.

C.I. m/z 498 [M+1]; $^1$H NMR (CDCl$_3$) δ7.61 (d, J=8.1 Hz, 1H), 7.53 (brs, 1H), 7.36 (d, 9.0 Hz, 1H), 7.04–7.33 (m, 8H), 6.52 (s, 1H), 6.21 (brs, 1H), 3.67 (s, 3H), 3.38 (s, 3H), 3.36 (s, 1H).

EXAMPLE 10

6-[(4-Chloro-phenyl)-hydroxy-(3-methyl-3H-imidazol-4-yl)-methyl]-1-methyl-4-(3-phenylethynyl-phenyl)-1H-quinolin-2-one The procedure was used as that of example 1 except that phenylacetylene was used in the place (trimethylsilyl) acetylene in step 1E to give the titled compound.

C.I. m/z 556 [M+1]; $^1$H NMR (CDCl$_3$) δ7.60 (dd, J=2.1, 8.8 Hz, 1H), 7.50 (m, 3H), 7.43 (brs, 1H), 7.21–7.37 (m, 9H), 7.17 (d, J=8.5 Hz, 2H), 7.08 (d, J=7.5 Hz, 1H), 6.61 (s, 1H), 6.26 (brs, 1H), 3.69 (s, 3H), 3.38 (s, 3H).

EXAMPLE 11

6-[(4-Chloro-phenyl)-hydroxy-(3-methyl-3H-imidazol-4-yl)-methyl]-4-[3-(4-hydroxy-but-1-ynyl)-phenyl]-1-methyl-1H-quinolin-2-one 11A. 6-(4-Chloro-benzoyl)-1-methyl-4-[3-(4-trityloxy-but-1-ynyl)-phenyl]-1H-quinolin-2-one 6-(4-Chloro-benzoyl)-4-[3-(4-hydroxy-but-1-ynyl)-phenyl]-1-methyl-1H-quinolin-2-one (1.41 g, 3.20 mMol), which was prepared by substituting 3-butyn-1-ol for (trimethylsilyl)acetylene in step 1E of example 1, and triethylamine (900 mL, 6.40 mMol) were dissolved in DCM (15 mL) under an atmosphere of dry $N_2$. To this solution was added triphenylmethyl chloride (980 mg, 3.50 mMol) and the mixture was stirred at ambient temperature for 4 hours. The reaction mixture was then partitioned between $Et_2O$/EtOAc and water. The organic layer was washed again with water and then with saturated aqueous $NaHCO_3$, dried over $MgSO_4$, filtered and concentrated under vacuum to give a white foam as the titled compound which was used without further purification.

11B. 6-[(4-Chloro-phenyl)-hydroxy-(3-methyl-3H-imidazol-4-yl)-methyl]4-[3-(4-hydroxy-but-1-ynyl)-phenyl]-1-methyl-1H-quinolin-2-one 2-Mercapto-1-methylimidazole (400 mg, 3.50 mMol) was dissolved in anhydrous THF (7.0 mL) under a stream of dry $N_2$. The solution was then cooled to −78° C. and a solution of 2.8 mL of a 2.5 M solution of n-butyllithium in hexanes was then added. After the addition was complete, the reaction mixture was warmed to ambient temperature and stirred at this temperature for 1 hour. The reaction mixture was then cooled to −78° C. and a solution of (4-chloro-benzoyl)-1-methyl-4-[3-(4-trityloxy-but-1-ynyl)-phenyl]-1H-quinolin-2-one in THF (7.0 mL) was added to the mixture. The reaction was warmed to ambient temperature and stirred overnight. The reaction mixture was quenched with saturated aqueous $NH_4Cl$ (25 mL) and partitioned between DCM and water. The DCM layer was dried over $Na_2SO_4$, filtered and concentrated under vacuum to give a green solid. The green solid was dissolved in 30 mL of acetic acid (AcOH) and the solution was cooled to about 5° C. To this solution was added 2.0 mL of 30% aqueous hydrogen peroxide ($H_2O_2$) dropwise. After the addition was complete, the reaction mixture was stirred at ambient temperature for 30 minutes. The reaction mixture was then cooled to 0° C., 200 mL of water was added and the reaction was basified to pH=10 with the slow addition of NaOH. Sodium sulfite was added portionwise until testing with starch-iodine paper showed no $H_2O_2$ left. The reaction mixture was partitioned between DCM and water. The DCM layer was dried over $Na_2SO_4$, filtered and concentrated under vacuum to give a green solid. The green solid was dissolved in a solution of MeOH/DCM (25:3) to which was added 3 N aqueous HCl (3.0 mL). The solution was then heated to 68° C. and reacted at this temperature for 2 hours. The solution was concentrated under vacuum to a thick sludge and then was partitioned between DCM and 0.01 N aqueous NaOH. The DCM layer was concentrated under vacuum and chromatographed on flash silica gel eluting with a gradient of MeOH/EtOAc/$NH_4OH$ (5:95:.01) to MeOH/EtOAc/$NH_4OH$ (10:90:.01) to give the titled compound.

C.I. m/z 524 [M+1]; $^1$H NMR (CDCl$_3$) δ7.53 (m, 1H), 7.43 (brs, 1H), 7.34 (d, J=7.9 Hz, 1H), 7.16–7.26 (m, 8H), 7.03 (d, J=7.5 Hz, 1H), 6.38 (s, 1H), 6.28 (s, 1H), 3.73 (m, 2H), 3.52 (s, 3H), 2.39 (s, 3H), 2.61 (m, 2H).

EXAMPLE 12

6-[(4-Chloro-phenyl)-hydroxy-(3-methyl-3H-imidazol-4-yl)-methyl]-1cyclopropylmethyl-4-(3-ethynyl-phenyl)-1H-quinolin-2-one 12A. 6-(4-Chloro-benzoyl)-1-cyclopropylmethyl-4-(3-iodo-phenyl)-1H-quinolin-2-one A solution of 6-(4-Chloro-benzoyl)-4-(3-iodo-phenyl)-1H-quinolin-2-one (9.68 g, 19.9 mmol), prepared as described in PCT international patent application publication number WO 97/21701 (published Jun. 19, 1997) (3.10 g, 7.87 mmol) in DMF (70 mL) was treated with cesium carbonate (23.1 g, 19.9 mmol) and (bromomethyl) cyclopropane (5.37 g, 39.8 mmol). The reaction mixture was stirred at room temperature for 12 hours, diluted with dichloromethane (75 mL), and washed with 1N HCl (2×50 mL) and brine (100 mL). The combined organic extracts were dried (MgSO$_4$), filtered, and concentrated in vacuo to give a black residue. Purification by flash column chromatography (silica, ethyl acetate:petroleum ether 1:9–3:7) gave 6-(4-Chloro-benzoyl)-1-cyclopropylmethyl-4-(3-iodo-phenyl)-1H-quinolin-2-one (6.79 g, 63%) as a yellow solid.

C.I. m/z 540 [M+1]; $^1$H NMR (CDCl$_3$): δ=8.05 (dd, J=9.0, 2.0 Hz, 1H), 7.92 (d, J=2.0 Hz, 1H), 7.80–7.77 (m,

2H), 7.71–7.64 (m, 3H), 7.50–7.46 (m, 2H), 7.37 (dd, J=7.8, 1.2 Hz, 1H), 7.22–7.17 (m, 1H), 6.68 (s, 1H), 4.32 (d, J=6.8 Hz, 2H), 1.34–1.23 (m, 1H), 0.64 –0.56 (m, 4H).

12B. 6-(4-Chloro-benzoyl)-1-cyclopropylmethyl-4-(3-trimethylsilanylethynyl-phenyl)-1H-quinolin-2-one A solution of 6-(4chloro-benzoyl)-1-cyclopropylmethyl-4-(3-iodo-phenyl)-1H-quinolin-2-one (4.0 g, 7.41 mmol) in DMF/diethylamine (1:1, 80 mL) was treated with palladium (II) bis(triphenyl)phosphine chloride (0.26 9, 0.37 mmol), trimethylsilylacetylene (1.09 g, 11.1 mmol), and copper (I) iodide (0.21 g, 1.09 mmol). The reaction mixture was stirred at room temperature for 3 hours, concentrated in vacuo, poured into $H_2O$ (450 mL), and filtered to give a crude brown foam. Purification by flash column chromatography (silica, ether:petroleum ether 1:1) gave 6-(4-Chloro-benzoyl)-1-cyclopropylmethyl-4-(3-trimethylsilanylethynyl-phenyl)-1H-quinolin-2-one (3.47 g, 92%) as a yellow solid.

C.I. m/z 510 [M+1]; $^1$H NMR ($CDCl_3$): δ=8.08 (dd, J=8.9, 1.9 Hz, 1H), 7.92 (d, J=1.7 Hz, 1H), 7.72–7.65 (m, 3H), 7.58–7.29 (m, 6H), 6.69 (s, 1H), 4.33 (d, J=7.1 Hz, 2H), 1.34–1.25 (m, 1H), 0.63–0.55 (m, 4H), 0.26 (s, 9H).

12C. 6-[(4-Chloro-phenyl)-hydroxy-(3-methyl-3H-imidazol-4-yl)-methyl]-1-cyclopropylmethyl-4-(3-ethynyl-phenyl)-1H-quinolin-2-one A solution of 2-(tert-butyl-dimethyl-silanyl)-1-methyl-1H-imidazole (1.71 g, 8.7 mmol) in THF (40 mL) at –78° C. was treated with sec-butyllithium (1.3 M in cyclohexane, 8.4 mL, 10.9 mmol). The reaction mixture was warmed to 0° C., stirred for 3 hours, and cooled to –78° C. A solution of 6-(4-Chloro-benzoyl)-1cyclopropylmethyl-4-(3-trimethylsilanylethynyl-phenyl)-1H-quinolin-2-one (3.47 g, 6.8 mmol) (2.87 g, 6.4 mmol) in THF (20 mL) was cannulated into the reaction mixture, slowly warmed to room temperature, and stirred overnight. The reaction mixture was quenched with ammonium chloride (12 mL), diluted with ether (200 mL), and washed with $H_2O$ (200 mL) and brine (200 mL). The organic layer was dried ($Na_2SO_4$), filtered, and concentrated in vacuo to give 6-[[2-(tert-Butyl-dimethyl-silanyl)-3 -methyl-3H-imidazol-4-yl]-(4-chloro-phenyl)-hydroxy-methyl]-1-cyclopropylmethyl-4-(3-trimethylsilanylethynyl-phenyl)-1H-quinolin-2one (4.50 g) as a yellow foam. The crude material was used in the next step without any further purification.

A solution of 6-[[2-(tert-Butyl-dimethyl-silanyl)-3-methyl-3H-imidazol-4-yl]-(4-chloro-phenyl)-hydroxy-methyl]-1-cyclopropylmethyl-4-(3-trimethylsilanylethynyl-phenyl)-1H-quinolin-2-one (4.50 g crude) in THF (100 mL) was treated with tetrabutylammonium chloride (1 M in THF, 10.0 mmol). The reaction mixture was stirred at room temperature for 12 hours, poured into $H_2O$ (200 mL), and extracted with ethyl acetate (3×100 mL). The combined organic extracts were washed with 1N HCl (100 mL), aqueous $NaHCO_3$ (100 mL), and brine (100 mL), dried ($MgSO_4$), filtered, and concentrated in vacuo to give a light green foam. Purification by flash column chromatography (silica, EtOAc:pet. ether:$NH_4OH$ 1:1:0.01) gave 6-[(4-Chloro-phenyl)-hydroxy-(3-methyl-3H-imidazol-4-yl)-methyl]-1-cyclopropylmethyl-4-(3-ethynyl-phenyl)-1H-quinolin-2-one (1.82 g, 51%) as a yellow powder.

C.I. m/z 520 [M+1]; $^1$H NMR ($CDCl_3$): δ=7.59 (dd, J=9.1, 2.1 Hz, 1H), 7.53–7.51 (m, 2H), 7.35–7.25 (m, 6H), 7.18–7.15 (m, 3H), 6.60 (s, 1H), 6.30 (s, 1H), 4.25 (d, J=7.1 Hz, 2H), 3.37 (s, 3H), 3.13 (s, 1H), 1.76 (br.s, 1H), 1.39–1.25 (m, 1H), 0.59–0.51 (m, 4H).

Separation of the Enantiomers of 6-[(4-Chloro-phenyl)-hydroxy-(3-methyl-3H-imidazol-4-yl)-methyl]-1-cyclopropylmethyl-4-(3ethynyl-phenyl)-1H-quinolin-2-one 6-[(4-Chloro-phenyl)-hydroxy-(3-methyl-3H-imidazol-4-yl)-methyl]-1-cyclopropylmethyl-4-(3-ethynyl-phenyl)-1H-quinolin-2-one (1.02 g) was separated into its enantiomers and purified by high-performance liquid chromatography over CHIRALCEL™ OD (manufactured by Daicel Chemical Industries, LTD, Osaka, Japan) (20 μm; eluent: hexane/isopropanol/diethylamine 65/35/0.1; 25° C.). Under these conditions, 0.42 g of the faster eluting enantiomer A was obtained and 0.43 g of the slower eluting enantiomer B. Both enantiomers were >97% optically pure.

EXAMPLE 13

6[Amino-(4-chloro-phenyl)-(3-methyl-3H-imidazol-4-yl)-methyl]-1-cyclopropylmethyl-4-(3-ethynyl-phenyl)-1H-quinolin-2-one The same procedure that was used in example 3 was followed except 6-[(4-Chloro-phenyl)-hydroxy-(3-methyl-3H-imidazol-4-yl)-methyl]-1-cyclopropylmethyl-4-(3-ethynyl-phenyl)-1H-quinolin-2-one (1.80 g, 3.5 mmol) was used in place of 6-[(4-Chloro-phenyl)-hydroxy-(3-methyl-3H-imidazol-4-yl)-methyl]-4-(3-ethynyl-phenyl)-1-methyl-1H-quinolin-2-one to give 6-[Amino-(4-chloro-phenyl)-(3-methyl-3H-imidazol-4-yl)-methyl]-1-cyclopropylmethyl-4-(3-ethynyl-phenyl)-1H-quinolin-2-one (1.12 g, 62%) as a yellow foam.

C.I. m/z 519 [M+1]; $^1$H NMR ($CDCl_3$): δ=7.57–7.51 (m, 3H), 7.43 (s, 1H), 7.36–7.31 (m, 2H), 7.26–7.22 (m, 2H), 7.18 (d, J=7.7 Hz, 1H), 7.09–7.05 (m, 3H), 6.63 (s, 1H), 6.32 (s, 1H), 4.28 (d, J=7.1 Hz, 2H), 3.39 (s, 3H), 3.13 (s, 1H), 2.11 (br.s, 2H), 1.31–1.27 (m, 1H), 0.61–0.52 (m, 4H).

EXAMPLE 14

6-[(4-Chloro-phenyl)-(3-methyl-3H-imidazol-4-yl)-[1,2,4]triazol-1-yl-methyl]-1-cyclopropylmethyl-4-(3-ethynyl-phenyl)-1H-quinolin-2-one The same procedure that was used in example 7 was followed except 6-[(4-chloro-phenyl)-hydroxy-(3-methyl-3H-imidazol-4-yl)-methyl]-1-cyclopropylmethyl-4-(3-ethynyl-phenyl)-1H-quinolin-2-one was used in place of 6-[(4-chloro-phenyl)-hydroxy-(3-methyl-3H-imidazol-4-yl)-methyl]-4-[3-(3,3dimethyl-but-1-ynyl)-phenyl]-1-methyl-1H-quinolin-2-one to give 6-[Chloro-phenyl)-(3-methyl-3H-imidazol-4-yl)-[1,2,4]triazol-1-yl-methyl]-1-cyclopropylmethyl-4-(3-ethynyl-phenyl)-1H-quinolin-2-one (21.0 mg, 55%) as a yellow film.

C.I. m/z 571 [M+1]; $^1$H NMR ($CDCl_3$): δ=8.06 (s, 1H), 7.89 (s, 1H), 7.56–7.52 (m, 3H), 7.34–7.25 (m, 5H), 7.14 (dd, J=7.8, 1.4 Hz, 1H), 7.04 (d, J=2.1 Hz, 1H), 6.95–6.91 (m, 2H), 6.66 (s, 1H), 6.55 (s, 1H), 4.26 (d, J=6.9 Hz, 2H), 3.14 (s, 1H), 3.06 (s, 3H), 1.30–1.23 (m, 1H), 0.61–0.52 (m, 4H); IR: $v_{max}$=3500, 1650, 1500, 1325, 1275, 1125, 1100, 1025 cm$^{-1}$.

What is claimed is:

1. A method for the treatment of abnormal cell growth in a mammal which comprises administering to said mammal a therapeutically effective amount of a compound of formula 1

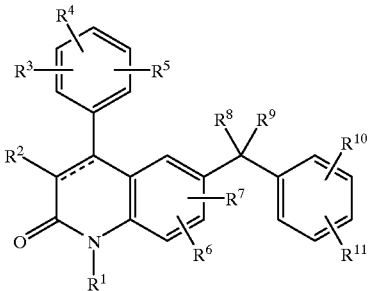

1 or a pharmaceutically acceptable salt, prodrug or solvate thereof wherein:

the dashed line indicates that the bond between C-3 and C-4 of the quinolin-2-one ring is a single or double bond;

$R_1$ is selected from H, $C_1$–$C_{10}$ alkyl, —$(CR^{13}R^{14})_qC(O)R^{12}$, —$(CR^{13}R^{14})_qC(O)OR^{15}$, —$(CR^{13}R^{14})_qOR^{12}$, —$(CR^{13}R^{14})_qSO_2R^{15}$, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein t is an integer from 0 to 5 and q is an integer from 1 to 5, said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;

$R^2$ is halo, cyano, —$C(O)OR^{15}$, or a group selected from the substituents provided in the definition of $R^{12}$;

each $R^3$, $R^4$, $R^5$, $R^6$, and $R^7$ is independently selected from H, $C_1$–$C_{10}$ alkyl, $C_2$–$C_{10}$ alkenyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC\equiv CR^{16}$, and wherein in the foregoing $R^3$, $R^4$, $R^5$, $R^6$, and $R^7$ groups t is an integer from 0 to 5; the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$OR^{12}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic), wherein t is an integer from 0 to 5;

$R^8$ is H, —$OR^{12}$, —$NR^{12}R^{12}$, —$NR^{12}C(O)R^{13}$, cyano, —$C(O)OR^{13}$, —$SR^{12}$, —$(CR^{13}R^{14})_t$(4–10 membered heterocyclic), wherein t is an integer from 0 to 5, or $C_1$–$C_6$ alkyl, wherein said heterocyclic and alkyl moieties are optionally substituted by 1 to 3 $R^6$ substituents;

$R^9$ is —$(CR^{13}R^{14})_t$(imidazolyl) wherein t is an integer from 0 to 5 and said imidazolyl moiety is optionally substituted by 1 or 2 $R^6$ substituents;

each $R^{10}$ and $R^{11}$ is independently selected from the substituents provided in the definition of $R^6$;

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein t is an integer from 0 to 5; said cycloalkyl, aryl and heterocyclic $R^{12}$ groups are optionally fused to a $C_6$–$C_{10}$ aryl group, a $C_514$ $C_8$ saturated cyclic group, or a 4–10 membered heterocyclic group; and the foregoing $R^{12}$ substituents, except H, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each $R_{13}$ and $R_{14}$ is independently H or $C_1$–$C_6$ alkyl, and where $R^{13}$ and $R^{14}$ are as —$(CR^{13}R^{14})_q$ or $(CR^{13}R^{14})_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$;

$R^{17}$, $R^{18}$ and $R^{19}$ are each independently selected from the substituents provided in the definition of $R^{12}$ except $R^{17}$, $R^{18}$ and $R^{19}$ are not H; and provided that at least one of $R^3$, $R^4$ and $R^5$ is —$(CR^{13}R^{14})_tC\equiv CR^{16}$ wherein t is an integer from 0 to 5 and $R^{13}$, $R^{14}$, and $R^{16}$ are as defined above, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

2. A pharmaceutical composition for the treatment of abnormal cell growth in a mammal which comprises a therapeutically effective amount of a compound of formula 1

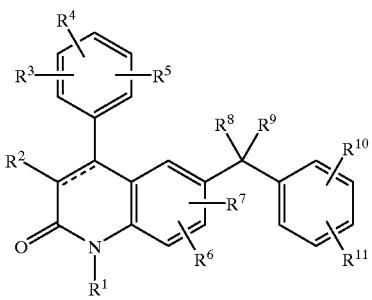

1 or a pharmaceutically acceptable salt, prodrug or solvate thereof wherein:

the dashed line indicates that the bond between C-3 and C-4 of the quinolin-2-one ring is a single or double bond;

R$^1$ is selected from H, C$_1$–C$_{10}$ alkyl, —(CR$^{13}$R$^{14}$)$_q$C(O) R$^{12}$, —(CR$^{13}$R$^{14}$)$_q$C(O)OR$^{15}$, —(CR$^{13}$R$^{14}$)$_q$OR$^{12}$, —(CR$^{13}$R$^{14}$)$_q$SO$_2$R$^{15}$, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic), wherein t is an integer from 0 to 5 and q is an integer from 1 to 5, said cycloalkyl, aryl and heterocyclic R$^1$ groups are optionally fused to a C$_6$–C$_{10}$ aryl group, a C$_5$–C$_8$ saturated cyclic group, or a 4–10 membered heterocyclic group; and the foregoing R$^1$ groups, except H but including any optional fused rings referred to above, are optionally substituted by 1 to 4 R$^6$ groups;

R$^2$ is halo, cyano, —C(O)OR$^{15}$, or a group selected from the substituents provided in the definition of R$^{12}$;

each R$^3$, R$^4$, R$^5$, R$^6$, and R$^7$ is independently selected from H, C$_1$–C$_{10}$ alkyl, C$_2$–C$_{10}$ alkenyl, halo cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2, —(CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$, and wherein in the foregoing R$^3$, R$^4$, R$^5$, R$^6$, and R$^7$ groups t is an integer from 0 to 5; the cycloalkyl, aryl and heterocyclic moieties of the foregoing groups are optionally fused to a C$_6$–C$_{10}$ aryl group, a C$_5$–C$_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O) OR$^{12}$, —OC(O)R$^{12}$, —NR$^{13}$C(O)OR$^{15}$, —NR$^{13}$C(O) R$^{12}$, —C(O)NR$^{12}$R$^{13}$, —NR$^{12}$R$^{13}$, —OR$^{12}$, C$_1$–C$_{10}$ alkyl, C$_2$–C$_{10}$ alkenyl, C$_2$–C$_{10}$ alkynyl, —(CR$^{13}$R$^{14}$)$_t$ (C$_6$–C$_{10}$ aryl), and —(CR$^{13}$R$^{14}$)$_t$(4–10 membered heterocyclic), wherein t is an integer from 0 to 5;

R$^8$ is H, —OR$^{12}$, —NR$^{12}$R$^{13}$, —NR$^{12}$C(O)R$^{13}$, cyano, —C(O)OR$^{13}$, —SR$^{12}$, —(CR$^{13}$R$^{14}$)$_t$(4–10 membered heterocyclic), wherein t is an integer from 0 to 5, or C$_1$–C$_6$ alkyl, wherein said heterocyclic and alkyl moieties are optionally substituted by 1 to 3 R$^6$ substituents;

R$^9$ is —(CR$^{13}$R$^{14}$)$_t$(imidazolyl) wherein t is an integer from 0 to 5 and said imidazolyl moiety is optionally substituted by 1 or 2 R$^6$ substituents;

each R$^{10}$ and R$^{11}$ is independently selected from the substituents provided in the definition of R$^6$;

each R$^{12}$ is independently selected from H, C$_1$–C$_{10}$ alkyl, —(CR$^{13}$R$^{14}$)$_t$(C$_3$–C$_{10}$ cycloalkyl), —(CR$^{13}$R$^{14}$)$_t$ (C$_6$–C$_{10}$ aryl), and —(CR$^{13}$R$^{14}$)$_t$(4–10 membered heterocyclic), wherein t is an integer from 0 to 5; said cycloalkyl, aryl and heterocyclic R$^{12}$ groups are optionally fused to a C$_6$–C$_{10}$ aryl group, a C$_5$–C$_8$ saturated cyclic group, or a 4–10 membered heterocyclic group; and the foregoing R$^{12}$ substituents, except H, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy C$_1$–C$_6$ alkyl, and C$_1$–C$_6$ alkoxy;

each R$^{13}$ and R$^{14}$ is independently H or C$_1$–C$_6$ alkyl, and where R$^{13}$ and R$^{14}$ are as —(CR$^{13}$R$^{14}$)$_q$ or (CR$^{13}$R$^{14}$)$_t$ each is independently defined for each iteration of q or t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^{19}$;

R$^{17}$, R$^{18}$ and R$^{19}$ are each independently selected from the substituents provided in the definition of R$^{12}$ except R$^{17}$, R$^{18}$ and R$^{19}$ are not H; and provided that at least one of R$^3$, R$^4$ and R$^5$ is —(CR$^{13}$R$^{14}$)$_t$C≡CR$^{16}$ wherein t is an integer from 0 to 5 and R$^{13}$, R$^{14}$, and R$^{16}$ are as define above, in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

3. A method for the treatment of an infection in a mammal, wherein said infection is facilitated by farnesyl protein transferase, which comprises administering to said mammal a therapeutically effective amount of a compound of formula 1

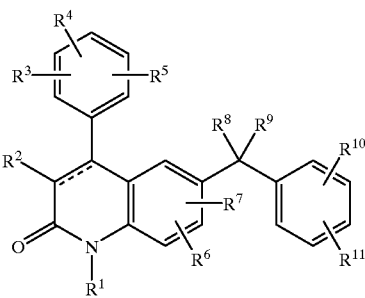

1 or a pharmaceutically acceptable salt, prodrug or solvate thereof wherein:

the dashed line indicates that the bond between C-3 and C-4 of the quinolin-2-one ring is a single or double bond;

R$^1$ is selected from H, C$_1$–C$_{10}$ alkyl, —(CR$^{13}$R$^{14}$)$_q$C(O) R$^{12}$, —(CR$^{13}$R$^{14}$)$_q$ C(O)OR$^{15}$, —(CR$^{13}$R$_{14}$)$_q$OR$^{12}$, —(CR$^{13}$R$^{14}$)$_q$SO$_2$R$^{15}$, —(CR$^{13}$R$^{14}$)$_t$(C$_{13}$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic), wherein t is an integer from 0 to 5 and q is an integer from 1 to 5, said cycloalkyl, aryl and heterocyclic R$^1$ groups are optionally fused to a C$_6$–C$_{10}$ aryl group, a C$_5$–C$_8$ saturated cyclic group, or a 4–10 membered heterocyclic group; and the foregoing R$^1$ groups, except H but including any optional fused rings referred to above, are optionally substituted by 1 to 4 R$^6$ groups;

R$^2$ is halo, cyano, —C(O)OR$^{15}$, or a group selected from the substituents provided in the definition of R$^{12}$;

each R$^3$, R$^4$, R$^5$, R$^6$, and R$^7$ is independently selected from H, C$_1$–C$_{10}$ alkyl, C$_2$–C$_{10}$ alkenyl, halo, cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2, —(CR$^{13}$R$^{14}$)$_t$(C$_6$–C$_{10}$ aryl), —(CR$^{13}$R$^{14}$) $_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$, and wherein in the foregoing R$^3$, R$^4$, R$^5$, R$^6$, and R$^7$ groups t is an integer from 0 to 5; the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)OR^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic), wherein t is an integer from 0 to 5;

$R^8$ is H, —$OR^2$, —$NR^{12}R^{13}$, —$NR^{12}C(O)R^{13}$, cyano, —$C(O)OR^{13}$, —$SR^{12}$, —$(CR^{13}R^{14})_t$(4–10 membered heterocyclic), wherein t is an integer from 0 to 5, or $C_1$–$C_6$ alkyl, wherein said heterocyclic and alkyl moieties are optionally substituted by 1 to 3 $R^6$ substituents;

$R^9$ is —$(CR^{13}R^{14})_t$(imidazolyl) wherein t is an integer from 0 to 5 and said imidazolyl moiety is optionally substituted by 1 or 2 $R^6$ substituents;

each $R^{10}$ and $R^{11}$ is independently selected from the substituents provided in the definition of $R^6$;

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t$($C_6$–$C_{10}$ aryl), and —$(CR^{13}R^{14})_t$(4–10 membered heterocyclic), wherein t is an integer from 0 to 5; said cycloalkyl, aryl and heterocyclic $R^{12}$ groups are optionally fused to a $C_6$–$C_{10}$ aryl group, a $C_5$—$C_8$ saturated cyclic group, or a 4–10 membered heterocyclic group; and the foregoing $R^{12}$ substituents, except H, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each $R^{13}$ and $R^{14}$ is independently H or $C_1$–$C_6$ alkyl, and where $R^{13}$ and $R^{14}$ are as —$(CR^{13}R^{14})_q$ or $(CR^{13}R^{14})_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$;

$R^{17}$, $R^{18}$ and $R^{19}$ are each independently selected from the substituents provided in the definition of $R^{12}$ except $R^{17}$, $R^{18}$ and $R^{19}$ are not H; and provided that at least one of $R^3$, $R^4$ and $R^5$ is —$(CR^{13}R^{14})_tC\equiv CR^{16}$ wherein t is an integer from 0 to 5 and $R^{13}$, $R^{14}$, and $R^{16}$ are as defined above, and a pharmaceutically acceptable carrier.

4. A pharmaceutical composition for the treatment of an infection in a mammal, wherein said infection is facilitated by farnesyl protein transferase, which comprises a therapeutically effective amount of a compound of formula 1

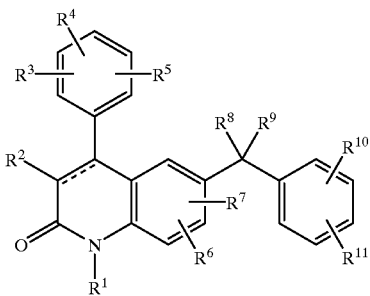

or a pharmaceutically acceptable salt, prodrug or solvate thereof wherein:

the dashed line indicates that the bond between C-3 and C-4 of the quinolin-2-one ring is a single or double bond;

$R^1$ is selected from H, $C_1$–$C_{10}$ alkyl, —$(CR^{13}R^{14})_qC(O)R^{12}$, —$(CR^{13}R^{14})_qC(O)OR^{15}$, —$(CR^{13}R^{14})_qOR^{12}$, —$(CR^{13}R^{14})_qSO_2R^{15}$, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein t is an integer from 0 to 5 and q is an integer from 1 to 5, said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;

$R^2$ is halo, cyano, —$C(O)OR^{15}$, or a group selected from the substituents provided in the definition of $R^{12}$;

each $R^3$, $R^4$, $R^5$, $R^6$, and $R^7$ is independently selected from H, $C_1$–$C_{10}$ alkyl, $C_2$–$C_{10}$ alkenyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14}-)_t(C_3$–$C_{10}$ cycloalkyl), and —$(CR^{13}R^{14})_tC\equiv CR^{16}$, and wherein in the foregoing $R^3$, $R^4$, $R^5$, $R^6$, and $R^7$ groups t is interger from 0 to 5; the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic), wherein t is an integer from 0 to 5;

$R^8$ is H, —$OR^{12}$, —$NR^{12}R^{13}$, —$NR^{12}C(O)R^{13}$, cyano, —$C(O)OR^{13}$, —$SR^{12}$, —$(CR^{13}R^{14})_t$(4–10 membered heterocyclic), wherein t is an integer from 0 to 5, or $C_1$–$C_6$ alkyl, wherein said heterocyclic and alkyl moieties are optionally substituted by 1 to 3 $R^6$ substituents;

$R^9$ is —$(CR^{13}R^{14})_t$(imidazolyl) wherein t is an integer from 0 to 5 and said imidazolyl moiety is optionally substituted by 1 or 2 $R^6$ substituents;

each $R^{10}$ and $R^{11}$ is independently selected from the substituents provided in the definition of $R^6$;

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein t is an integer from 0 to 5; said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each $R^{13}$ and $R^{14}$ is independently H or $C_1$–$C_6$ alkyl, and where $R^{13}$ and $R^{14}$ are as —$(CR^{13}R^{14})_q$ or $(CR^{13}R^{14})_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$;

$R^{17}$, $R^{18}$ and $R^{19}$ are each independently selected from the substituents provided in the definition of $R^{12}$ except $R^{17}$, $R^{18}$ and $R^{19}$ are not H; and provided that at least one of $R^3$, $R^4$ and $R^5$ is —$(CR^{13}R^{14})_tC\equiv CR^{16}$ wherein t is an integer from 0 to 5 and $R^{13}$, $R^{14}$, and $R^{16}$ are as defined above, and a pharmaceutically acceptable carrier.

5. The method of claim 3 wherein said infection is hepatitus delta virus or malaria.

6. The pharmaceutical composition of claim 4 wherein said infection is hepatitus delta virus or malaria.

\* \* \* \* \*